United States Patent [19]
Schindele et al.

[11] Patent Number: 5,494,793
[45] Date of Patent: Feb. 27, 1996

[54] MONOMERIC PHTHALOCYANINE REAGENTS

[75] Inventors: Deborah C. Schindele; Barry V. Pepich; George E. Renzoni, all of Seattle; Karen L. Fearon, Woodinville; Niels H. Andersen; Thomas H. Stanton, both of Seattle, all of Wash.

[73] Assignee: British Technology Group USA Inc., Gulph Mills, Pa.

[21] Appl. No.: 366,971

[22] Filed: Jun. 14, 1989

Related U.S. Application Data

[63] Continuation-in-part of Ser. No. 241,608, Sep. 8, 198803, and a continuation-in-part of Ser. No. 309,453, Feb. 10, 198903, which is a continuation-in-part of Ser. No. 61,937, Jun. 12, 1987, abandoned, which is a continuation-in-part of Ser. No. 941,619, Dec. 15, 1986, abandoned, and a continuation-in-part of Ser. No. 946,475, Dec. 24, 1986, Pat. No. 4,803,170.

[51] Int. Cl.$^6$ .................... C12Q 1/68; G01N 33/53; C12N 9/00; C07H 21/04
[52] U.S. Cl. ................. 435/6; 435/7.1; 435/183; 536/24.3
[58] Field of Search ............ 435/6, 7, 7.1; 436/800; 540/122, 127; 536/27, 24.3

[56] References Cited

U.S. PATENT DOCUMENTS

| | | | |
|---|---|---|---|
| 2,613,128 | 10/1952 | Baumann | 8/28 |
| 4,160,645 | 7/1979 | Ullman | 23/230 B |
| 4,193,983 | 3/1980 | Ullman et al. | 424/12 |
| 4,220,450 | 9/1980 | Maggio | 23/230 B |
| 4,233,402 | 11/1980 | Maggio et al. | 435/7 |
| 4,235,869 | 11/1980 | Schwarzberg | 424/8 |
| 4,256,834 | 3/1981 | Zuk et al. | 435/7 |
| 4,277,437 | 7/1981 | Maggio | 422/61 |
| 4,318,707 | 3/1982 | Litman et al. | 23/230 B |
| 4,483,929 | 11/1984 | Szoka | 436/533 |
| 4,540,660 | 9/1985 | Harte et al. | 435/7 |
| 4,540,670 | 9/1985 | Arai et al. | 436/170 |
| 4,560,534 | 12/1985 | Kung et al. | 422/68 |
| 4,614,723 | 9/1986 | Schmidt et al. | 436/536 |
| 4,650,770 | 3/1987 | Liu et al. | 436/523 |
| 4,656,129 | 4/1987 | Wagner | 435/7 |
| 4,816,386 | 3/1989 | Gotoh et al. | 430/495 |

FOREIGN PATENT DOCUMENTS

| | | |
|---|---|---|
| 63852A3 | 3/1982 | European Pat. Off. . |
| 142369A2 | 5/1985 | European Pat. Off. . |

OTHER PUBLICATIONS

*The Phthalocyanines* 1:127, 1983.
Hara, T., et al., Immunoassay using a metal–complex compound as a chemiluminescent catalyst. II. An improvement of the analytical method for practical use, *Bull. Chem. Soc. Jpn.* 56:2965–2968, 1983.
Hara, T., et al., Immunoassay using a metal–complex compound as a chemiluminescent catalyst. I. Iron(III) phthalocyanine as a labeling reagent, *Bull. Chem. Soc. Jpn.* 56:2267–2271, 1983.
Hara, T., et al., Immunoassay using a metal–complex compound as a chemiluminescent catalyst. III. Flow–through analysis of a labeled antigen bound by immune reaction, *Bull. Chem. Soc. Jpn.* 57:587–588, 1984.
Hara, T., et al., Immunoassay using a metal–complex compound as a chemiluminescent catalyst. IV. The investigation of a metal porphine complex as a labeling reagent, *Bull. Chem. Soc. Jpn.* 57:3009–3010, 1984.
Hara, T., et al., Immunoassay using a metal–complex compound as a chemiluminescent catalyst. V. Continuous immunoassay by the use of CLCCIA, *Bull. Chem. Soc. Jpn.* 58:1299–1303, 1985.
Mew, D., et al., Photoimmunotherapy: treatment of animal tumors with tumor–specific monoclonal antibody–hematoporphyrin conjugates, *J. Immunol.* 130(3):1473–1477, 1983.
Mew, D., et al., Ability of specific monoclonal antibodies and conventional antisera conjugated to hematoporphyrin to label and kill selected cell lines subsequent to light activation, *Cancer Research* 45:4380–4386, September 1985.
Ben–Hur, E., and I. Rosenthal, The phthalocyanines: a new class of mammalian cells photosensitizers with a potential for cancer phototherapy, *Int. J. Radiat. Biol.* 47(2):145–147, 1985.

(List continued on next page.)

*Primary Examiner*—Stephanie W. Zitomer
*Attorney, Agent, or Firm*—Christensen, O'Connor, Johnson & Kindness

[57] ABSTRACT

Fluorescent and/or chromogenic reagents in which a phthalocyanine derivative is monomerically conjugated with an antigen, antibody, oligonucleotide, or nucleic acid. Methods are presented in in which greater than 90% of the phthalocyanine dyes are monomeric when conjugated. This greatly enhances their performance as detectable markers in immunoassays, nucleic acid probe assays, immunoblotting, hybridization assays, microscopy, imaging, flow cytometry, DNA sequencing, and photodynamic therapy. For use as fluorophores, the free base phthalocyanine may or may not be metallated. Metals for fluorescent phthalocyanine include aluminum, silicon, phosphorus, gallium, germanium, cadmium, scandium, magnesium, tin, and zinc. For use as chromogens, the phthalocyanine may or may not be metallated. For use in aqueous solution, the phthalocyanine macrocycle should be derivatized with water-solubilizing substituents such as sulfonic acid, phosphate, phosphonate, hydroxy, phenoxy, amino, ammonium, or pyridinium groups. To promote disaggregation, metallation with an atom of ≠valence or higher is recommended, so that the monomer will take on an axial ligand in aqueous solution. For use in enzymatic immunoassays and enzymatically enhanced nucleic acid probe assays, the monomeric phthalocyanine derivative is conjugated via an enzyme-cleavable linkage with the antigen, antibody, oligonucleotide, or nucleic acid. Reversibly quenched embodiments are also provided in which a cleavable linkage joins a fluorescent phthalocyanine monomer with another phthalocyanine, a heavy metal, or a paramagnetic species.

8 Claims, 10 Drawing Sheets

OTHER PUBLICATIONS

Ben–Hur, E., and I. Rosenthal, Photosensitized inactivation of Chinese hamster cells by phthalocyanines, *Photochem. and Photobiol.* 42(2):129–133, 1985.

Ben–Hur, E., and I. Rosenthal, Factors affecting the photokilling of cultured Chinese hamster cells by phthalocyanines, *Radiat. Res.* 103:403–409, 1985.

Brasseur, N., et al., Biological activities of phthalocyanines III. Photoinactivation of V–79 Chinese hamster cells by tetrasulfophthalocyanines, *Photochem. and Photobiol.* 42(5):515–521, 1985.

Ben–Hur, E., and I. Rosenthal, Action spectrum (600–700 nm) for chloraluminum phthalocyanine–induced phototoxicity in Chinese hamster cells, *Lasers in the Life Sciences* 1(1):79–86, 1986.

Ben–Hur, E., and I. Rosenthal, Photosensitization of Chinese hamster cells by water–soluble phthalocyanines, *Photochem. and Photobiol.* 43(6):615–619, 1986.

Chan, W–S., et al., Cell uptake, distribution and response to aluminium chloro sulphonated phthalocyanine, a potential anti–tumor photosensitizer, *Br. J. Cancer* 53:255–263, 1986.

Rosenthal, I., et al., The role of molecular oxygen in the photodynamic effect of phthalocyanines, *Radiat. Res.* 107:136–142, 1986.

Selman, S. H., et al., Photodynamic treatment of transplantable bladder tumors in rodents after pretreatment with chloroaluminum tetrasulfophthalocyanine, *J. Urology* 136:141–145, 1986.

Ben–Hur, E., et al., Effect of light fluence rate on mammalian cells photosensitization by chloroaluminium phthalocyanine tetrasulphonate, *Int. J. Radiat. Biol.* 51(3):467–476, 1987.

Jori, G., et al., Factors governing the mechanism and efficiency of porphyrin–sensitized photooxidations in homogeneous solutions and organized media, in Porphyrin Photosensitization, D. Kessel and T. J. Dougherty, eds., Plenum Press, New York, pp. 193–212, 1981.

Spikes, J. D., and J. C. Bommer, Zinc tetrasulphophthalocyanine as a photodynamic sensitizer for biomolecules, *Int. J. Radiat. Biol.* 50(1):41–45, 1986.

Spikes, J. D., Phthalocyanines as photosensitizers in biological systems and for the photodynamic therapy of tumors, *Photochem. and Photobiol.* 43(6):691–699, 1986.

Langlois, R., et al., Biological activities of phthalocyanines–IV. Type II sensitized photooxidation of L–tryptophan and cholesterol by sulfonated metallo phthalocyanines, *Photochem. and Photobiol.* 44(2):117–123, 1986.

Ben–Hur, E., et al., Phthalocyanine photosensitization of mammalian cells: biochemical and ultrastructural effects, *Photochem. and Photobiol.* 46(5):651–656, 1987.

Brasseur, N., et al., Biological activities of phthalocyanines—VII. Photoinactivation of V–79 Chinese hamster cells by selectively sulfonated gallium phthalocyanines, *Photochem. and Photobiol.* 46(5):739–744, 1987.

Singer, C. R. J., et al., Phthalocyanine photosensitization for in vitro elimination of residual acute non–lymphoblastic leukaemia: preliminary evaluation, *Photochem. and Photobiol.* 46(5):745–749, 1987.

Tralau, C. J., et al., Aluminum sulfonated phthalocyanine distribution in rodent tumors of the colon, brain and pancreas, *Photochem. and Photobiol.* 46(5):777–781, 1987.

Chan, W.–S., et al., Photodynamic therapy of a murine tumor following sensitisation with chloro aluminum sulfonated phthalocyanine, *Photochem. and Photobiol.* 46(5):867–871, 1987.

Rosenthal, I., et al., The effect of substituents on phthalocyanine photocytotoxicity, *Photochem. and Photobiol.* 46(6):959–963, 1987.

Gruen, L. C., The aggregation of copper phthalocyanine dyes, *Aust. J. Chem.* 25:1661–1667, 1972.

Blagrove, R. J., The aggregation of the tetrasodium salt of copper phthalocyanine–4,4',4",4'''-tetrasulphonic acid: diffusion studies, *Aust. J. Chem.* 26:1545–1549, 1973.

Sheppard, S. E., and A. L. Geddes, Effect of solvents upon the absorption spectra of dyes. IV. Water as solvent: a common pattern, *J. Amer. Chem. Soc.* 66(12):1995–2002, 1944.

Sheppard, S. E., and A. L. Geddes, Effect of solvents upon the absorption spectra of dyes. V. Water as solvent: quantitative examination of the dimerization hypothesis, *J. Amer. Chem. Soc.* 66(12):2003–2009, 1944.

Bernauer, K., and S. Fallab, Phtalocyanine in wässeriger Lösung I, *Helv. Chim. Acta* 44(5):1287–1292, 1961.

Darwent, J. R., et al., Excited singlet and triplet state electron– transfer reactions of aluminium(III) sulphonated phthalocyanine, *J. Chem. Soc., Faraday Trans. 2*, 78:347–357, 1982.

Weber, J. H., and D. H. Busch, Complexes derived from strong field ligands. XIX. Magnetic properties of transition metal derivatives of 4,4',4",4'''-tetrasulfophthalocyanine, *Inorg. Chem.* 4(4):469–471, 1965.

Fukada, N., Phthalocyanine derivatives. IV. Salts of cobalt 4,4' ,4",4'''-phthalocyaninetetrasulfonic acid, *Nippon Kagaku Zasshi*, 75:1141–1143, 1954 (Abstract).

Elvidge, J. A., et al., Conjugated macrocycles. Part XXIX. Tribenzotetrazaporphin metal derivatives and dibromotribenzotetrazaporphin, *J. Chem. Soc.*, 2466–2472, 1957.

Blakeslee, D., and M. G. Baines, Immunofluorescence using dichlorotriazinylaminofluorescein (DTAF). I. Preparation and fractionation of labeled IgG, *J. Immunol. Meth.* 13:305–320, 1976.

Cook, C. E., et al., Theophylline radioimmunoassay: synthesis of antigen and characterization of antiserum, *Res. Comm. Chem. Pathol. Pharmacol.* 13(3):497–505, 1976.

Hara, T., et al., Immunoassay using a metal–complex compound as a chemiluminescent catalyst. I. Iron(III) Phthalocyanine as a labeling reagent, *Chemical Abstracts* 99:320, Abstract 172173u, 1983.

Hara, T., et al., Immunoassay using a metal–complex compound as a chemiluminescent catalyst. V. Continuous immunoassay by the use of CLCCIA, *Chemical Abstracts* 103:301, Abstract 84292c, 1985.

Elvidge, J. A., et al., Conjugated macrocycles. Part XXXIX. Tribenzotetrazaporphin metal derivatives and dibromotribenzotetrazaporphin, *J. Chem. Soc.*, pp. 2466–2472, 1957.

Gurevich, M. G., and K. N. Solov'ev, Luminescence of rare earth phthalocyanines, *Chemical Abstracts* 57:15948, 1962.

MacKay, A. G., et al., Preparation and properties of some rare–earth phthalocyanines, *Aust. J. Chem.* 27:955–964, 1974.

Harriman, A., and M–C. Richoux, Attempted photoproduction of hydrogen using sulphophthalocyanines as chromophores for three–component systems, *J.C.S. Faraday II* 76:1618–1626, 1980.

Winkelman, J. W., and G. H. Collins, Neurotoxicity of tetraphenylporphinesulfonate $TPPS_4$ and its relation to photodynamic therapy, *Photochem. and Photobiol.* 46(5):801–807, 1987.

Rowley, G. L., et al., Sensitive fluoroimmunoassays for feritin and IgE, Paper No. 18, AACC Conference, Oakridge, San Antonio, TX, 1987.

MONOMERIC PHTHALOCYANINE REAGENTS

This application is a continuation-in-part of application Ser. No. 241,608, filed Sep. 8, 1988 (abandoned), and is a continuation-in-part of international application No. PCT/US87/03226, filed Dec. 11, 1987, and is a continuation-in-part of application Ser. No. 309,454, filed Feb. 10, 1989 (abandoned), which is a continuation of Ser. No. 061,937, filed Jun. 12, 1987 (abandoned), which is a continuation-in-part of application Ser. No. 941,619, filed Dec. 15, 1986 (abandoned), and is a continuation-in-part of application Ser. No. 946,475, filed Dec. 24, 1986 (U.S. Pat. No. 4,803,170), the benefits of the filing dates of which are claimed under 35 U.S.C. §120.

FIELD OF THE INVENTION

The invention provides water-soluble phthalocyanine compounds that are monomerically conjugated to biochemical moieties such as antibodies, antigens, oligonucleotides, nucleic acids, or enzyme-cleavable ligands for use either as detectable reagents in immunoassays, nucleic acid probe assays, immunoblotting or hybridization techniques, enzyme-based assays, DNA sequencing, flow cytometry, microscopy, fluorescence imaging, or as therapeutic reagents for directed cell killing (photodynamic therapy).

BACKGROUND OF THE INVENTION

The phthalocyanine pigments are a group of light-fast organic pigments with four isoindole groups, $(C_6H_4)C_2N$, linked by four nitrogen atoms to form a cyclic conjugated chain. Included are phthalocyanine (blue-green), copper phthalocyanine (blue), chlorinated copper phthalocyanine (green), and sulfonated copper phthalocyanine (green). These pigments are commonly used in enamels, plastics, linoleum, inks, wallpaper, fabrics, paper, and rubber goods.

Free base phthalocyanine, and aluminum, cadmium, magnesium, silicon, tin, and zinc metallated phalocyanines are reported to be fluorescent; see *The Phthalocyanines* 1:127, 1983. One or more of these species have been utilized in or proposed for semiconductors, organic dyes, stain removing agents, bactericides, and optical coatings. For example, European patent publication No. 142,369 discloses the use of certain phthalocyanine derivatives for hematology, specifically to differentiate basophils from other blood cells. U.S. Pat. No. 4,816,386 discloses a near-infrared-sensitive phthalocyanine-polymer composition comprising a substituted aluminum phthalocyanine and a polymer wherein substituted aluminum phthalocyanine dimers and/or dimer aggregates, which are reportedly responsible for the near-infrared sensitivity, are included.

Phthalocyanines have been reported for potential use in various types of immunoassays. See: U.S. Pat. No. 4,160,645 (at column 18, lines 18 to 22); U.S. Pat. No. 4,193,983 (at column 16, lines 36 to 39); U.S. Pat. No. 4,220,450 (at column 17, lines 23 to 26); U.S. Pat. No. 4,233,402 (at column 24, lines 53 to 56); U.S. Pat. No. 4,235,869 (at column 11, line 67 to column 12, line 2); U.S. Pat. No. 4,256,834 (at column 21, lines 34 to 36); U.S. Pat. No. 4,277,437 (at column 17, lines 11 to 14); U.S. Pat. No. 4,318,707 (at column 9, lines 14 to 16); U.S. Pat. No. 4,483,929 (at column 6, lines 36 to 39); U.S. Pat. No. 4,540,660; U.S. Pat. No. 4,540,670 (at column 11, lines 40 to 59); U.S. Pat. No. 4,560,534 (at column 5, line 67 to column 6, line 7); U.S. Pat. No. 4,650,770 (at column 18, lines 22 to 25); U.S. Pat. No. 4,656,129; and European patent publication No. 63,852 A3 (at page 31, lines 30 to 33). However, no mention is made of reactive forms of the phthalocyanine molecule which can be covalently coupled to a member of a ligand-binding partner.

Phthalocyanine derivatives have been employed as catalysts in chemiluminescence immunoassay systems. See: Hara, T., et al., *Bull. Chem. Soc. Jpn.* 56:2965–2968, 1983; Hara, T., et al., *Bull. Chem. Soc. Jpn.* 56:2267–2271, 1983; Hara, T., et al., Bull. Chem. Soc. Jpn. 57:587–588, 1984; Hara, T., et al., *Bull. Chem. Soc. Jpn.* 57:3009–3010, 1984; and Hara, T., et al., *Bull. Chem. Soc. Jpn.* 58:1299–1303, 1985. Hara described a chemiluminescence complex catalyst immunoassay in which iron phthalocyanine serves as the catalyst for a chemiluminescent reaction between luminol and hydrogen peroxide. The chemiluminescent signal is quantitated and correlated with the amount of analyte present in the test sample. Hara examined a number of phthalocyanine (Fe, Co) and porphyrin (Fe, Pd, Pt, Mn, Sn) complexes and reported that iron phthalocyanine exhibits the greatest catalytic activity and provides the highest sensitivities for this type of assay. Although Hara et al. describes a method for the covalent coupling of porphyrin and phthalocyanine complexes to proteins, the resultant product is highly aggregated. From spectral data contained in *Bull. Chem. Soc. Jpn.* 56:2965–2968, it is possible to calculate that the most monomerically labeled protein in this work contains less than 10% phthalocyanine monomer.

Phthalocyanines have also been suggested for use in photodynamic therapy (PDT), which is a radiation therapy for cancer that utilizes a photosensitive agent (sensitizer) and visible light as the radiation source. The sensitizer must be selectively delivered to the tumor tissues; for example, monoclonal antibody-hematoporphyrin conjugates have been reported. See: Mew, D., et al., *J. Immunol.* 130(3):1473–1477, 1983; and Mew, D., et al., *Cancer Research* 45:4380–4386, 1985. Thereafter, activation of the sensitizer by visible light kills the cells by a photodynamic reaction involving singlet oxygen generation. The phthalocyanines, particularly the aluminum and zinc tetrasulfonate derivatives, have been suggested for use in PDT, based upon their use as photosensitizers for cultured mammalian cells. See: Ben-Hur, E., and I. Rosenthal, *Int. J. Radiat. Biol.* 47:145–147, 1985; Ben-Hur, E., and I. Rosenthal, *Photochem. and Photobiol.* 42:129–133, 1985; Ben-Hur, E., and I. Rosenthal, *Radiat. Res.* 103:403–409, 1985, Brasseur, N., et al., *Photochem. and Photobiol.* 42:515–521, 1985; Ben-Hur, E., and I. Rosenthal, *Lasers in the Life Sciences* 1:79–86, 1986; Ben-Hur, E., I. Rosenthal, *Photochem. and Photobiol.* 43:615–621, 1986; Chan, W. S., et al., *Br. J. Cancer* 53:255–263, 1986; Rosenthal, I., et al., *Radiat. Res.* 107:136–142, 1986; Selman, S. H., et al., *J. Urology* 136:141–145, 1986; Ben-Hur, E., et al., *Int. J. Radiat Biol.* 51:467–476, 1987; Jori, G., et al., in Porphyrin Photosensitization, D. Kessel and T. J. Dougherty, eds., Plenum Press, New York, pp. 193–212, 1981; Spikes, J. D., and J. C. Bommer, *Int. J. Radiat. Biol.* 50(1):41–45, 1986; Spikes, J. D., *Photochem. and Photobiol.* 43(6):691–699, 1986; Langlois, R., et al., Photochem. and *Photobiol.* 44(2):117–123, 1986; Ben-Hur, E., et al., *Photochem. and Photobiol.* 46(5):651–656, 1987; Brasseur, N., et al., *Photochem. and Photobiol.* 46(5):739–744, 1987; Singer, C. R. J., et al., *Photochem. and Photobiol.* 46(5):745–749, 1987; Tralau, C. J., et al., *Photochem. and Photobiol.* 46(5):777–781, 1987; Chan, W.-S., et al., *Photochem. and Photobiol.* 46(5):867–871, 1987; and Rosenthal, I., et al., *Photochem. and Photobiol.* 46(6):959–963, 1987. Of these, the following are considered to be the most pertinent.

Jori et al. (1981) address factors governing porphyrin sensitized photooxidations in various media. The efficiency of photooxidation was determined to be dependent upon the composition of the solvent in which the oxidation occurs.

Spikes and Bommer (1986) describe the photoproperties of zinc tetrasulfophthalocyanine in aqueous media. In water, the zinc derivative is aggregated and is incapable of photosensitization. In the presence of a cationic detergent, the zinc derivative disaggregates and becomes an efficient photosensitizer.

Langlois et al. (1986) observe the monomeric nature of sulfonated phthalocyanines of aluminum and gallium in water. Both were found to be efficient photosensitizers.

Pursuant to the present disclosure, while some metallo sulfonated phthalocyanines may be monomeric in water, it is not possible to covalently couple them to carriers such as proteins or oligonucleotides. The reactive form of the preferred sulfonated phthalocyanines are not soluble or monomeric in water. Monomerism of the reactive form of the phthalocyanine prior to and during covalent coupling is absolutely necessary to produce conjugates which bear monomerically tethered phthalocyanines.

Other fluorescent compounds (fluorophores) have been widely used in immunoassays, flow cytometry, and fluorescence microscopy. U.S. Pat. No. 4,614,723 is of interest for disclosing water-soluble porphyrin derivatives as label molecules for fluorescence immunoassays. The coupling of the disclosed porphyrin derivatives to immunologically active materials is reportedly carried out in the customary manner, e.g., with a water-soluble carbodiimide derivative.

It is also noteworthy that the most sensitive enzymatic immunoassays employ fluorogenic rather than colorimetric substrates. Three well-known fluorogenic enzyme substrate couples are: alkaline phosphatase (AP) and 4-methylumbelliferylphosphate (MUP); β-galactosidase (β-Gal) and 4-methylumbelliferyl-D-galactopyranoside (MUG); and horseradish peroxidase (HRP) and p-hydroxyphenyl acetic acid (HPA). Generally, the AP, β-Gal, and HRP systems are useful for detection of analytes at concentrations greater than $10^{-15}$ M. To date, the sensitivity of these systems is limited by the spectral properties of the generated fluorophores.

Also of interest are prior publications concerning aggregation of phthalocyanines in solution, and the effects of solvents upon the absorption spectra of dyes generally. See: Gruen, L. C., Aust. J. Chem. 2,5:1661–1667, 1972; Blagrove, R.J., Aust. J. Chem. 26:1545–1549, 1973; Sheppard, S. E., and A. L. Geddes, J. Amer. Chem. Soc. 66(12):1995–2002, 1944; Sheppard, S. E., and A. L. Geddes, J. Amer. Chem. Soc. 66(12):2003–2009, 1944; Bernauer, K., and S. Fallab, Helv. Chim. Acta 44(5):1287–1292, 1961; and Darwent, J. R., et al., J. Chem. Soc., Faraday Trans. 2, 78:347–357, 1982. Of these, the following are considered to be the most pertinent.

Blagrove (1973) investigated the effect of urea and thiourea on the aggregation of copper phthalocyanine tetrasulfonic acid in water. Both were shown to disaggregate the dye in aqueous solution.

Gruen (1972) studied the visible absorbance spectra of two copper phthalocyanine dyes as a function of concentration, temperature, pH, ionic strength, and solvent composition. The data indicate an equilibrium between monomeric and dimeric dye exists. The equilibrium was most effected by the dielectric strength of the solvent systems studied, as the amount of monomer increased with decreasing dielectric constant.

Darwent et al . (1982) describe the photophysical properties of aluminum sulfophthalocyanine. No aggregation of the dye was observed in water over the concentration range studied.

Pursuant to the present disclosure, we have determined that the reactive form of aluminum phthalocyanine required for covalent coupling is neither soluble nor monomeric in water. The use of urea, thiourea, or organic solvents alone are insufficient for monomeric coupling. The reactive dye is optimally coupled to biological molecules as disclosed below in Examples 3 and 4. The composition of the reaction mixture including ingredients and concentration as well as timing and temperature are critical for achieving monomeric conjugation.

SUMMARY OF THE INVENTION

The invention provides fluorescent and/or chromogenic reagents in which a phthalocyanine derivative is monomerically conjugated with an antigen, antibody, oligonucleotide, or nucleic acid. The monomeric as opposed to dimeric or more highly aggregated nature of the phthalocyanine moiety is critical to preserving the emissivity and/or absorptivity of the phthalocyanine in the reagent, and hence its signal strength and the sensitivity of an assay in which the subject reagents are employed. Methods are presented in which greater than 90% of the phthalocyanine dyes are monomeric when conjugated. This greatly enhances their performance as detectable markers in immunoassays, nucleic acid probe assays, immunoblotting, hybridization assays, microscopy, imaging, flow cytometry, DNA sequencing, and photodynamic therapy.

For use as a fluorophore, the free base phthalocyanine may or may not be metallated. Metals for fluorescent phthalocyanines include aluminum, silicon, phosphorus, gallium, scandium, germanium, cadmium, magnesium, tin, and zinc. For use as chromogens, the phthalocyanine may or may not be metallated. For use in aqueous solution, the phthalocyanine macrocycle should be derivatized with water-solubilizing substituents such as sulfonic acid, sulfonate, carboxylic acid, carboxylate, phosphoric acid, phosphate, phosphonate, hydroxy, phenoxy, amino, ammonium, and pyridinium groups. To promote disaggregation, metallation with an atom of +valence or higher is recommended, so that the monomer will take on an axial ligand in aqueous solution. Other methods for prevention of aggregation include conjugation in reaction media containing disaggregating organic solvents (such as dimethylformamide or dimethyl sulfoxide), preincubation of the phthalocyanine in disaggregating medium prior to conjugation, and/or indirect conjugation with the use of tethers containing spacer groups of two or more atoms.

The subject reagents are useful as detectable markers in immunoassays, enzyme-based assays, nucleic acid probe assays, hybridization or immunoblotting techniques, DNA sequencing, flow cytometry, fluorescence imaging, and microscopy. For use in immunoassays, the monomeric phthalocyanine derivative is conjugated either directly or indirectly to the antigen, oligonucleotide, nucleic acid, or antibody of interest. For use in enzymatic immunoassays and enzymatically enhanced nucleic acid probe assays, the monomeric phthalocyanine derivative is conjugated via an enzyme-cleavable linkage with the antigen, antibody, oligonucleotide, or nucleic acid. Reversibly quenched embodiments, in which a cleavable linkage joins a fluorescent phthalocyanine monomer to another phthalocyanine, a heavy metal, or a paramagnetic species, are also provided for use as reporting groups in such assays.

DETAILED DESCRIPTION OF THE PREFERRED EMBODIMENT

Figure 1:
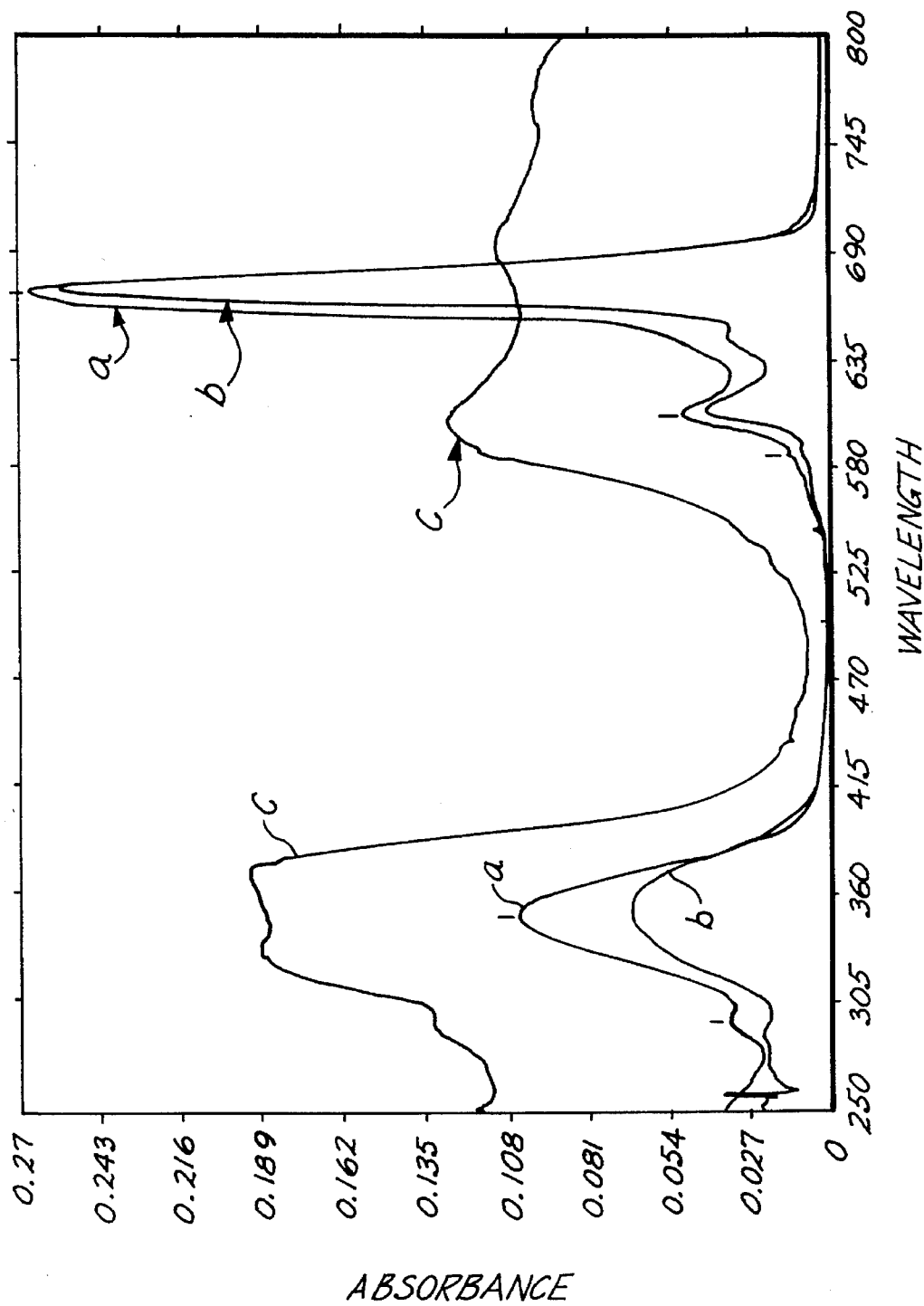
FIG. 1 presents the visible absorption spectra of aluminum phthalocyanine trisulfonate in water (plot a), as compared with aluminum phthalocyanine in dimethyl sulfoxide (plot b) and in water (plot c)

In one aspect, the invention provides an improved fluorescent reagent for use in analytical procedures such as immunoassays, enzyme-based assays, nucleic acid probe assays, hybridization or immunoblotting techniques, DNA sequencing, flow cytometry, microscopy, and fluorescence imaging by which the presence and typically the quantity of some chemical, biochemical, or biological analyte is determined, often in a physiological fluid like blood plasma or urine or in matrices such as acrylamide or nitrocellulose. An ideal fluorophore for such assays would have a high fluorescence quantum yield, a large Stokes shift (>50 nm), and an emission at wavelengths greater than 600 nm. A high quantum efficiency ensures that the excitation light employed in the analytical procedure is converted efficiently into detectable emission. A large Stokes shift permits discrimination between actual signal and contaminating signal derived from Raman, Rayleigh, and Tyndall light scatter. Emission at wavelengths greater than 600 nm eliminates background fluorescence (typically from about 350 to about 600 nm) attributable to endogenous fluorophores (e.g., serum proteins, bilirubin, NADH) present in physiological fluids and to reagent and cuvette impurities.

By way of example, the following Table compares the excitation wavelength (EX), emission wavelength (EM), Stokes shift, and quantum yield (QY) of four fluorophores that have been used in such analytical procedures: 6,6'-dihydroxy(1,1'-diphenyl)-3,3'-diacetic acid (DBDA); 4-methylumbelliferone (MUN); fluorescein (F); and rhodamine B (R-B).

| Fluorophore | EX | EM | Stokes Shift | QY |
|---|---|---|---|---|
| DBDA | 320 nm | 410 nm | 90 nm | — |
| MUN | 360 nm | 448 nm | 88 nm | 0.5 |
| F | 495 nm | 525 nm | 30 nm | 0.5 |
| R-B | 596 nm | 620 nm | 24 nm | 0.6 |

Referring to the Table, DBDA and MUN lack optimal fluorescence properties for use in physiological assays, as both emit at wavelengths less than 500 nm. Fluorescein also emits at well below 600 nm, and furthermore has a Stokes Shift less of than 50 nm. Rhodamine B emits at greater than 600 nm but has a Stokes shift of less than 50 nm. Use of a fluorophore with improved spectral characteristics would make existing assay systems more sensitive.

The invention provides such improved fluorescent reagents in the form of water-soluble, monomerically tetherable phthalocyanine derivatives according to formula 1

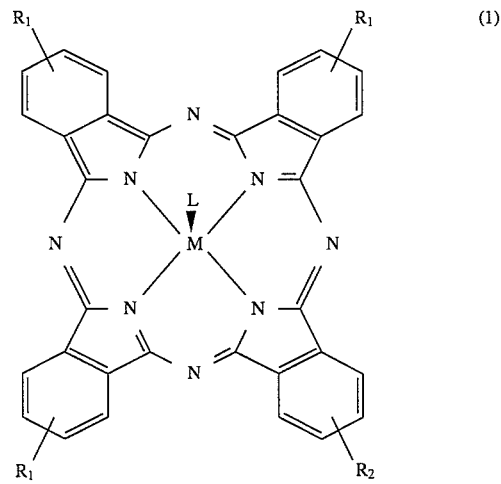

wherein, as described below, M indicates two hydrogen atoms or a metal atom selected from among aluminum, silicon, phosphorus, gallium, germanium, cadmium, magnesium, tin, zinc, and scandium; $R_1$ indicates substituents that provide water solubility; substituent $R_2$ may likewise enhance water solubility and provides a linkage or point of linkage suitable for conjugation to another reagent moiety, or is a cleaved residue of such a linkage; and L may be one or more axial ligands. For divalent metals (M), Cd, Mg, Zn, no axial ligand (L) is present. Trivalent metal atoms (M), Al, Ga, Sc, have at least one axial ligand (L). Tetravalent metal atoms (M), Si, Ge, Sn, have at least two axial ligands (L). Phosphorus will bear either one or three axial ligands (L).

Figure 2:
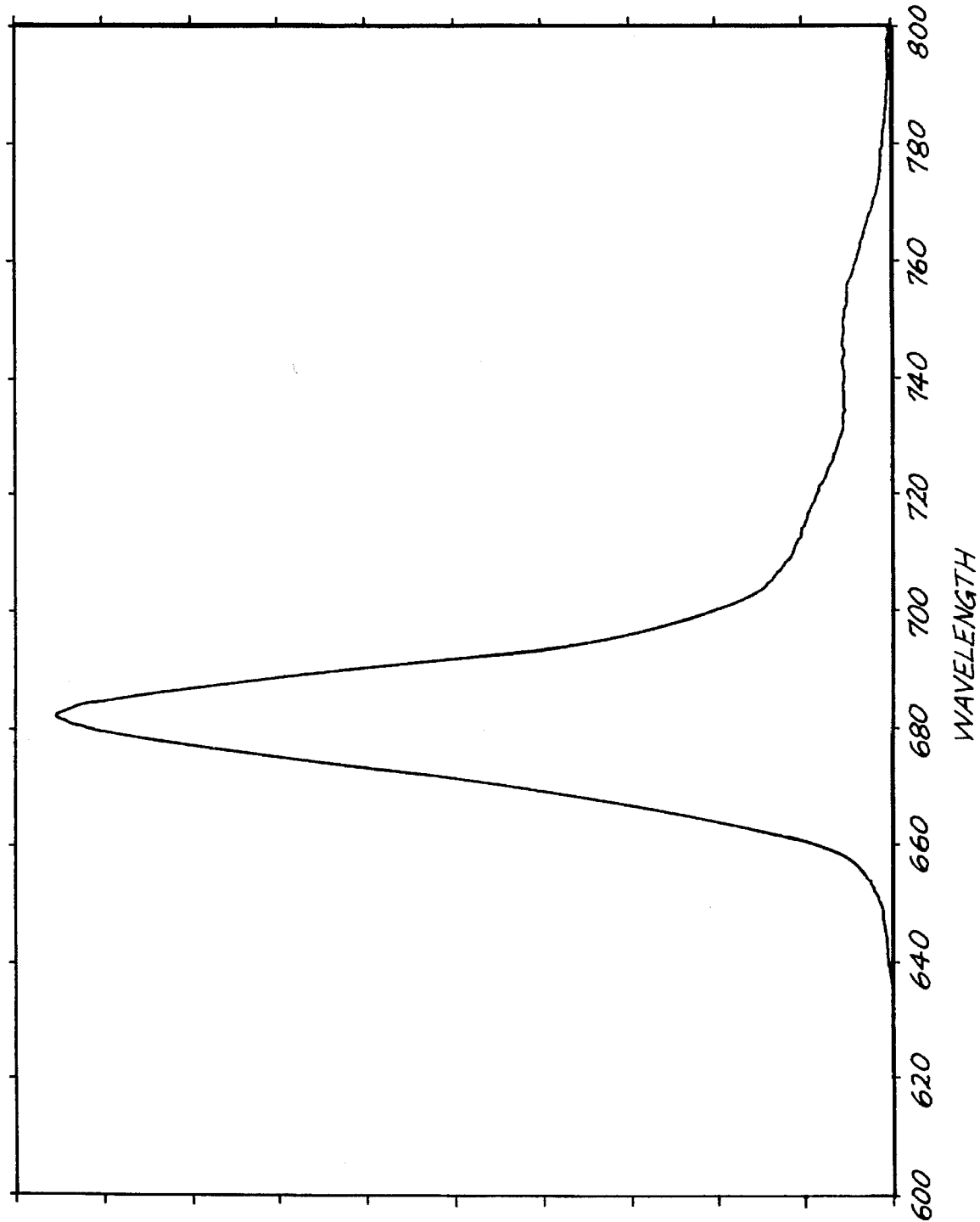
FIG. 2 presents the emission spectrum of aluminum phthalocyanine trisulfonate in water.
Figure 3:
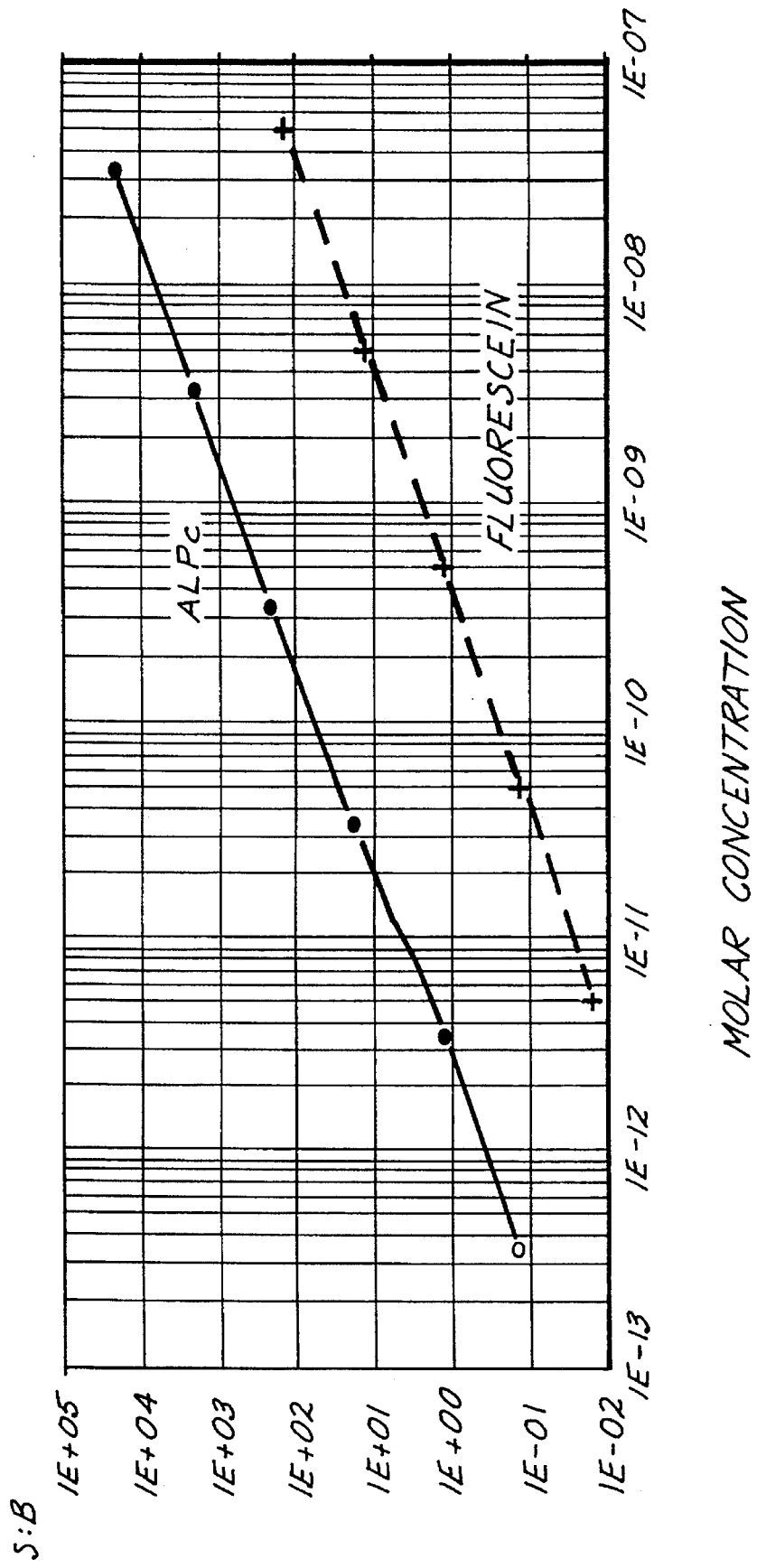
FIG. 3 presents a linear dynamic range comparison of hydrolyzed fluorescein isothiocyanate in basic water and aluminum phthalocyanine trisulfonate in water.

As a family of fluorophores, the metallophthalocyanines are characterized by a very narrow and strong absorption in the red envelope centered around 670 nm ($E_o$=230,000) and a broad and less intense absorption ($E_o$60,000) at around 350 nm in organic solvents (see FIG. 1, trace b). Referring to FIG. 2, the emission wavelength (680 nm) of the trisulfonate derivative of aluminum phthalocyanine 1, elicited by excitation at 350 nm, is red-shifted from the emissions of endogenous fluorophores in physiological solutions. The red emission wavelength of 1 is one of the greatest advantages of this fluorophore. Since emission is shifted away from that of endogenous fluorescence (400–600 nm), background is reduced. Reduction of background leads to a higher signal-to-background ratio and greater sensitivity. This advantage may be realized regardless of where excitation is effected so long as there is absorbance at the excitation wavelength. Excitation of 1 at 325 nm (helium cadmium laser), around 350 nm (Hg lamp source or argon ion laser), 633 nm (helium neon laser), 647 nm (krypton ion laser), or 670 nm (diode laser) leads to emission at 680 nm. A second advantage arises when one excites in the ultraviolet. Excitation of 1 at 325 nm or approximately 350 nm leads to emission with more than a 300 nm Stokes shift. This Stokes shift leads to further reduction in background and even greater sensitivity. Fluorescence measurements indicate that aluminum phthalocyanine trisulfonate 1 is detectable at concentrations as low as $10^{-15}$ M. Linear dynamic range studies indicate a working range of over nine decades and superior detection limits when compared to fluorescein and rhodamine B. FIG. 3 shows a comparison of the signal-to-background of 1 versus a hydrolyzed form of fluorescein. Red emission of 1 coupled with the advantage of a large Stokes shift leads to a 100-fold increase in signal-to-background relative to that of fluorescein.

Since aluminum phthalocyanine compounds 1 possess spectral properties superior to those observed for DBDA, MUN, F, and R-B, use of an aluminum phthalocyanine species can provide more sensitive assays than those employing the aforementioned species. However, to be an effective marker in biological systems, the aluminum phthalocyanine derivative 1 must be rendered soluble and disaggregated in aqueous environments and furthermore must be conjugated in monomeric form in the reagent.

The following "R" substituents ($R_1$ and/or $R_2$) bound to the phthalocyanine macrocycle 1 can serve as suitable water-solubilizing moieties: sulfonic acid groups ($-SO_3H$), sulfonate groups ($-SO_3^-$, $X^+$), carboxylic acid groups ($-CO_2H$), carboxylate groups ($-CO_2^-$, $X^+$), phosphoric acid groups ($-PO_4H_2$), phosphate groups ($-PO_4^{--}$, $2X^+$), phosphonate groups ($-PO_3H$ or $-PO_3^-$, $X^+$), hydroxy or phenoxy groups ($-OH$), amino groups ($-NH_2$), and ammonium and pyridinium groups ($-NR_4^+$, $X^-$). The greater the number of the R groups on derivative 1, the greater the resultant water solubility. In particular, sulfonate groups $R_1, R_2$ render the compound 1 soluble over a wide range of pH's (pH=2–12). Carboxylic acid groups are more sensitive to pH than sulfonic acid groups, thus limiting the versatility and performance of the former in aqueous systems. Below pH 5, carboxylic acid groups are not ionized, which limits the solubility of such markers. Both sulfonic and phosphoric acids are ionized below pH 2.

In the following discussion, the water-soluble and highly emissive aluminum phthalocyanine tri- and tetrasulfonates are presented as representative models for the subject group of fluorescent water-soluble metallated phthalocyanine derivatives 1. As described below in Example 1, the sulfonated aluminum phthalocyanines can be prepared by sulfonation of aluminum phthalocyanine, by metallation of free base phthalocyanine, or by total synthesis. The tri- and tetrasulfonated derivatives can serve as water-soluble precursors for preparing many of the other derivatives 1.

Figure 4:
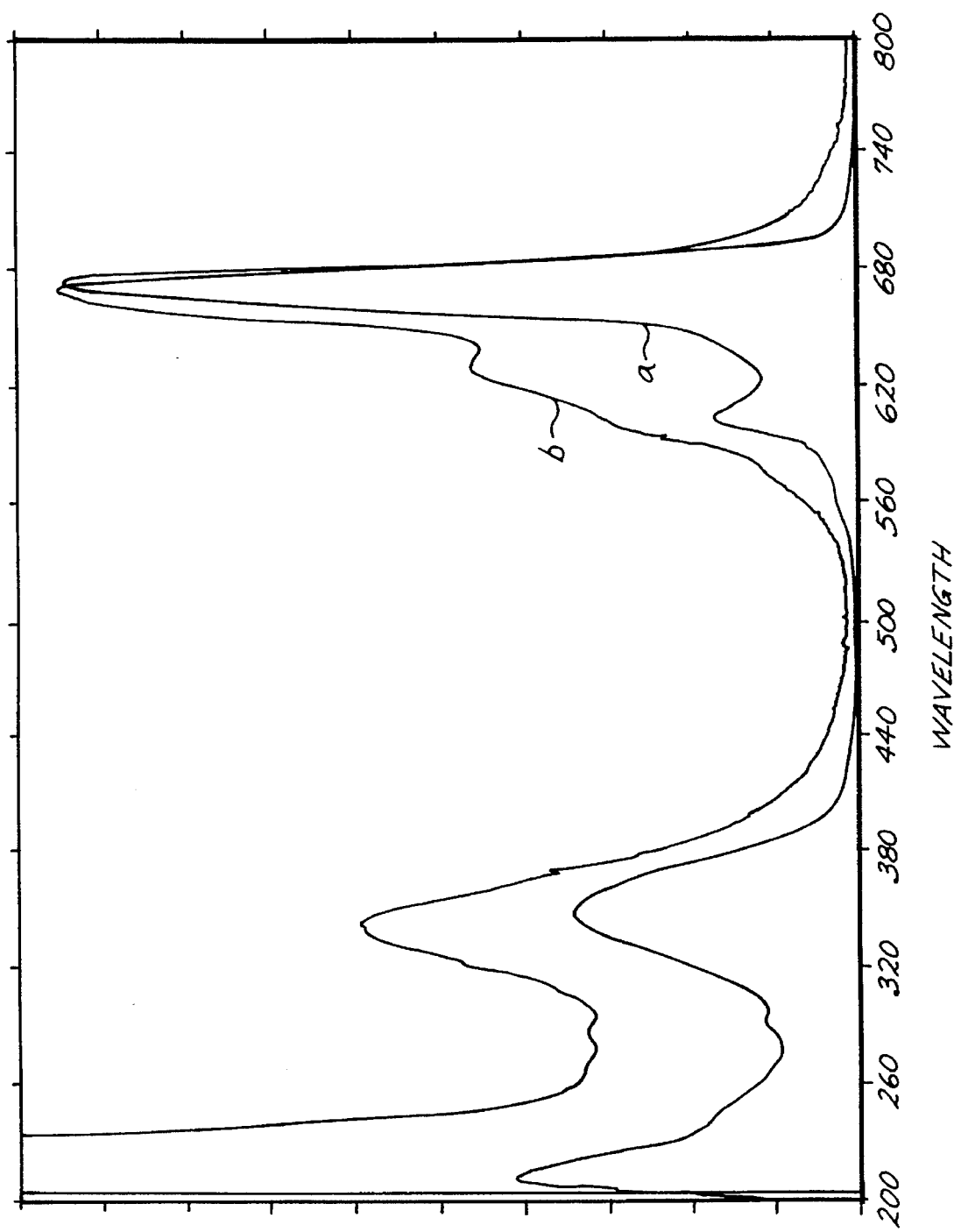
FIG. 4 presents the visible absorption spectra of aluminum phthalocyanine trisulfonate (plot a) as compared to zinc phthalocyanine trisulfonate in phosphate buffered saline (plot b)

Because of the hydrophobic nature of the phthalocyanine macrocycle, most water-soluble phthalocyanine species exhibit a strong tendency toward aggregation. For example, the parent aluminum phthalocyanine compound 1 (wherein $R_1$ and $R_2$ are H, and L is $-OH$) is nicely monomeric in solvents like pyridine, dimethylformamide (DMF), dimethylsulfoxide (DMSO), and methanol but is very highly aggregated and poorly soluble in water. In contrast, aluminum phthalocyanine trisulfonate suffers little aggregation in aqueous solution. Referring again to FIG. 1, the visible absorption spectra of the parent aluminum phthalocyanine in DMSO (plot b) and in water (c) are compared to the trisulfonated derivative 1 in water (a). Upon sulfonation the red absorption at 670 nm is reduced ($E_0 = 150,000$), while the quantum yield (0.6) and the blue absorption remain unchanged. Trace (a) is an example of a monomeric absorbance spectrum for aluminum phthalocyanine trisulfonate in water. Two factors are considered to be responsible. First, aluminum phthalocyanine trisulfonate is highly charged in aqueous solution, which tends to electrostatically inhibit self-association. Second, the aluminum atom in aluminum phthalocyanine trisulfonate bears an axial ligand "L" (probably $-OH$ in water) which prevents the "plate-like" stacking so prevalent with metallo(II)phthalocyanines and also porphyrins. This is supported by FIG. 4 which compares the visible absorption spectra for the Zn and Al phthalocyanine trisulfonates in phosphate buffered saline. Zinc does not have an axial ligand, and hence the zinc phthalocyanine trisulfonate (trace b) shows a strong absorption at 648 nm corresponding to the dimer. From the molar extinction of the dimer ($E_0 = 250,000$) it is possible to conclude that over 35% of the ZnPc molecules are aggregated. As the quantum yield for the dimer is much less than 0.001, this leads to greater than a 35% reduction in the brightness of the ZnPc solution relative to the AlPc solution.

The effect of the axial ligand (L) on solubility is indicated by the observation that hydroxyaluminum phthalocyanine but not chloraluminum phthalocyanine is soluble in polar, protic solvents such as methanol. To enhance water solubility, L should be $-OZ$ or $-NZ_2$ wherein Z is selected from among hydrogen, alkyl, acyl, and silyl groups, the latter three preferably being charged.

The quantum yield of aluminum phthalocyanine trisulfonate is approximately 0.6 in its monomeric state but diminishes to less than 4% (0.02) of its original value when aggregated. The monomeric versus dimeric (or more highly aggregated) nature of the aluminum phthalocyanine reagent is thus critical to the fluorescence emissivity and hence the signal strength and sensitivity of the assay.

To recapitulate, the high quantum yield and monomeric nature of molecule 1 are partly attributable to the aforementioned R groups and also to the central aluminum atom, which takes on an axial ligand that serves to enhance solubility and hinder the onset of aggregation. Furthermore, the central aluminum exhibits no notable heavy atom effect, which has been shown in other molecules to decrease fluorescence. It is contemplated that other metal atoms (M) with + valences or higher may take on an axial ligand(s) in the phthalocyanine macrocycle, thereby conferring a similar resistance to aggregation in aqueous solution. For use as fluorescent species, the metal should be diamagnetic and have a lower atomic weight than that of bromine, so as to avoid a heavy-atom quenching effect; suitable metal atoms for the latter purpose include aluminum, silicon, phosphorus, gallium, germanium, scandium, and tin. As a comparative example, the fluorescence quantum yield of copper(II)phthalocyanine trisulfonate is more than 200 times less than that of aluminum(III)phthalocyanine trisulfonate; this difference arises from aggregation and an enhancement of spin orbital coupling due to the paramagnetism of copper. Both processes give rise to radiationless deactivation of the excited state and serve to decrease the fluorescent quantum yield.

In order to determine the effect of the central metal atom on phthalocyanine emission, we prepared a series of metallated phthalocyanines. A summary of the correlations between periodic table group, atomic mass, and fluorescence quantum yield (QY) are shown in the Table below. Representative synthesis protocols for preparation of metallated phthalocyanines are disclosed in Example 1.

| Metal | Group | Atomic Mass | Relative QY |
|---|---|---|---|
| Zn | 2B | 65.4 | 0.48 |
| Al | 3B | 27.0 | 1.00 |
| Ga | 3B | 69.7 | 0.62 |
| Sc | 3A | 45.0 | 0.91 |
| Si | 4B | 28.1 | 0.88 |
| Ge | 4B | 02.6 | 0.78 |

Examination of the results presented in the Table above show that low atomic mass metals in Group 3 or higher yield metallated phthalocyanines with greater emissivity.

For commercial applications, the aluminum phthalocyanine species should be both chemically and photochemically stable. Phthalocyanines are an extremely stable class of chemical compounds, and aluminum phthalocyanine is particularly so. The phthalocyanines are thermally stable, and are often purified by sublimation at temperatures greater than 400° C. Chemically, the phthalocyanines are resistant to acidic or basic hydrolysis, oxidation, and reduction. In contrast to some metallophthalocyanines, aluminum(III)phthalocyanine is not subject to a change in oxidation state and shows no measurable tendency for demetallation. Aluminum phthalocyanine trisulfonate is also photochemically inert; with its high quantum yield of fluorescence, nearly all of its excited state energy is dissipated by emission. In addition, a study of the relative absorbance and fluorescence behavior of the sulfonated analog of aluminum phthalocyanine showed invariant physical properties over a wide range of pH conditions (pH=4–13).

Aluminum phthalocyanine and related compounds can be readily prepared from commercially available materials. The parent compound (as aluminum phthalocyanine chloride) is available from Kodak and from Strem Chemical Company. The free base phthalocyanine tetrasulfonate can be purchased from Porphyrin Products, P.O. Box 31, Logan, Utah 84321. The precursors for total synthesis may be purchased from a wide variety of sources, including Aldrich, Kodak, and Tokyo Chemical Industry Company (Tokyo Kasei Incorporated), Portland, Ore.

Aluminum phthalocyanine derivatives that are monomeric in aqueous media can be prepared by selection of the type and number of the macrocycle functional groups R. For example, the introduction of polar or highly charged functional groups such as sulfonates tends to make aluminum phthalocyanine more water soluble and less aggregated than the corresponding carboxylated or hydroxylated species. Generally, the greater the number of polar functional groups ($R_1$ and $R_2$), the less the aggregation of the corresponding aluminum phthalocyanine derivative. For example, a tri- or tetrasulfonated aluminum phthalocyanine is more water soluble and shows less tendency toward aggregation than the corresponding mono- or disulfonated species. The more homogeneous the derivative, the greater the tendency toward aggregation. For example, a single isomer of aluminum phthalocyanine tetrasulfonate will be more aggregated than a mixture of the four isomeric tetrasulfonate derivatives.

The aluminum phthaloeyanine core 1 can be readily and reproducibly functionalized to yield a water-soluble, reactive species for conjugation to proteins and other reagent moieties. For this purpose, sulfonamide, amide, ether, and thioether linkages are preferred. In other words, substituent $R_2$ can bear any amino, carboxy, thiol, or hydroxy functionality; or $R_2$ can bear the linked analyte or other reagent moiety directly. To assure that the monomeric aluminum phthalocyanine species 1 remain monomeric, the reagent moieties should be conjugated in a medium that contains disaggregating organic solvents such as DMF or DMSO. For conjugation of aluminum phthalocyanine to proteins, such organic solvents should make up 10–20% of the reaction medium. Use of a maximum percentage of the organic solvent dimethylformamide (DMF) is preferred. The maximum allowable organic is determined by the stability of the protein. For stable proteins such as streptavidin, 20% DMF is preferred. For more sensitive materials such as antibodies, 10% DMF is preferred. For coupling of aluminum phthalocyanine to smaller molecules, such organic solvents should make up 20–100% of the medium. Again, a maximum amount of the organic solvent DMF is preferred. The maximum allowable organic is determined by the solubility of the species to be labeled. For coupling small DMF-soluble organic molecules, 100% DMF is preferred. For coupling to aqueous soluble species such as oligonucleotides, 20% DMF is preferred. Representative synthesis protocols for tethering analogs of aluminum phthalocyanine are disclosed in Examples 2, 3, and 4. In an improved method for conjugation, a reactive derivative of aluminum phthalocyanine (but not the protein) is incubated in a disaggregating organic solvent (e.g., 100% DMF) for one or more hours prior to attachment to a protein. A representative protocol for this coupling method is disclosed in Example 4.

Representative moieties to which such a reactive aluminum phthalocyanine can be conjugated include small physiological analytes such as drugs (therapeutic and abused), drug metabolites (e.g., cotinine), hormones, peptides, nucleotides, neurotransmitters, cholesterol, probes, oligonucleotides, and tether linkers. A representative synthesis is presented in Example 3. Exemplary intermediate-size physiological analytes include hormones (e.g., thyroid-stimulating hormone), growth factors (e.g., nerve growth factor), oligonucleotides (cDNA, DNA, RNA, and synthetic oligonucleotide fragments), and peptides. The subject phthalocyanines can likewise be conjugated monomerically to larger reagent moieties such as antibodies, antigen-binding fragments, serum proteins, enzymes, polynucleotides (DNA, RNA), intracellular organelles, cell surface antigens, etc.

In use, the subject monomeric phthalocyanine reagents, due to their superior fluorescence properties, can be advantageously employed as detectable markers in immunoassays. By way of comparison, applications that employ fluorescein as a detector marker are limited in sensitivity by the high background interference attributable to Tyndall, Rayleigh, or Raman scatter and endogenous fluorescence. The red emission of aluminum phthalocyanine coupled with the large Stokes shift essentially eliminate these sources of background.

Aluminum phthalocyanine may be utilized for competitive, displacement, or sandwich immunoassays, or immunoblotting techniques. In such embodiments, the fluorophore may be coupled to either the antigen or antibody. For maximum sensitivity, one or more phthalocyanine moieties must be coupled to the antigen or antibody of interest in a monomeric fashion. The more monomeric or disaggregated the phthalocyanine, the more emissive the labeled species. Assay sensitivity is directly proportional to emissivity.

Much of the foregoing discussion has been directed to monomeric versus dimeric and aggregated forms of phthalocyanines. For example, in FIG. 4 we compared Al and Zn phthalocyanine trisulfonates and discussed the formation of phthalocyanine dimers, which lead to the quenching of fluorescence. The trisulfonated species, due to their asymmetry and number of possible isomers, have a lower tendency to form dimers than the more symmetric tetrasulfonates made via the total synthesis method (see Example 1). Trends in aggregation of the trisulfonates are very complex and involve a continuum of aggregate sizes and orientations. Despite this, we have found an empirical relationship that relates the spectroscopic properties (in terms of the relative heights of the maximum blue and red absorbance peaks) of phthalocyanines to their relative quantum yield.

Figure 5:
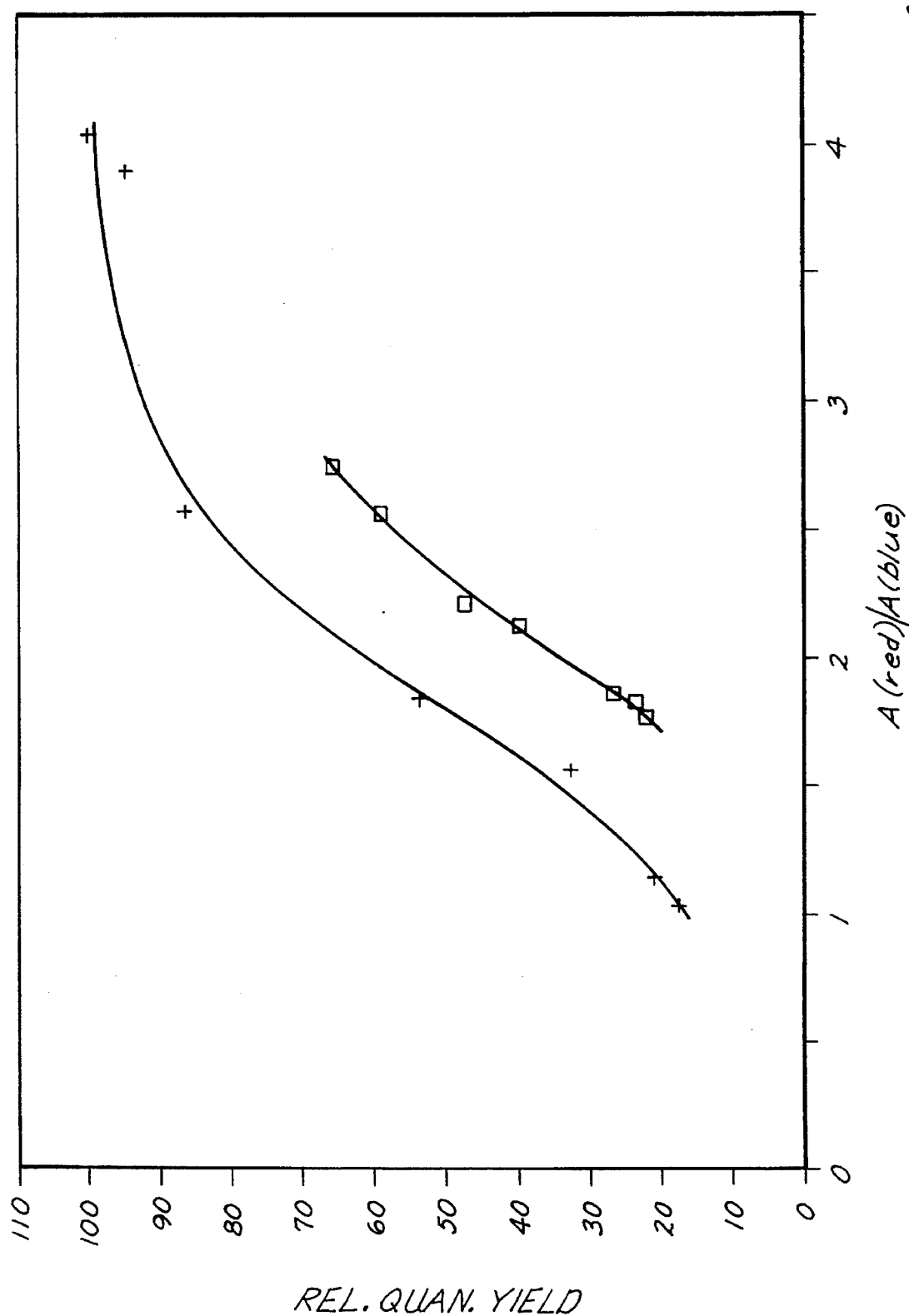
FIG. 5 empirically relates the ratio of the phthalocyanine red and blue absorbances with the relative fluorescent quantum yield.

Early in our investigations we observed that the blue absorbance of the phthalocyanines was independent of the state of aggregation and hence the emission yield. In contrast, the onset of aggregation can be followed by changes in the red absorption band. In FIG. 5 we show a plot of the ratio of the red absorbance (680 nm) to the absorbance in the blue (350 nm), [A(red)/A(blue)], versus the relative emission yield for unconjugated (+) and conjugated (squares) forms of AlPc. Here the data points corresponding to the unconjugated dye were obtained by preparing a number of solutions which contained differing percentages of pyridine in water to effect the state of aggregation. The points corresponding to conjugated dye correspond to different protein conjugates made via one of the preferred methods of conjugation.

Figure 6:
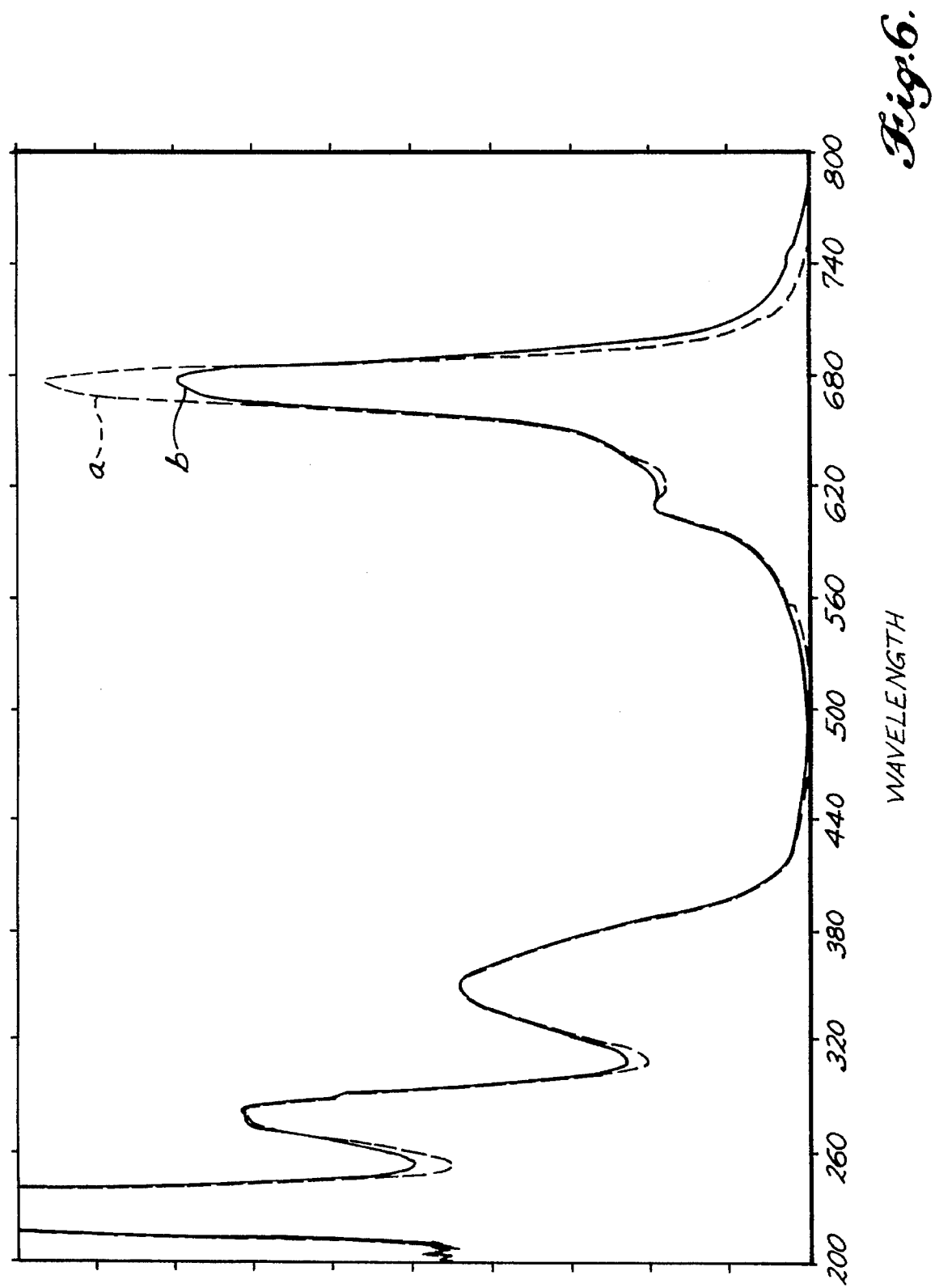
FIG. 6 presents the visible absorbance spectra for two AlPc-streptavidin conjugates with identical dye loadings prepared by two different methods.

We note for FIG. 5 that in both cases the A(red)/A(blue) ratio decreases with decreasing relative quantum yield. In addition, the behavior of the protein-bound dye is shifted toward a lower relative quantum yield, but very nicely parallels the free dye in solution. This shift or decrease in quantum yield arises from the hydrophobic nature of the protein environment rather than aggregation quenching. This interpretation is supported by further findings that the small molecule conjugates (see Example 3) lie on the line corresponding to the free dye. To illustrate this effect we present an overlay of two protein conjugates in FIG. 6. Trace (a) corresponds to Example 4D in the Table below, and trace (b) to 4C. It is evident from the blue region that the amount of protein (278 nm absorbance) and aluminum phthalocyanine (350 nm absorbance) are identical in each trace. In trace (b) we see a decrease in the red maximum, a slight increase in the dimer absorbance (648 nm), and a tailing on the long wavelength side associated with higher aggregates. In accordance with the empirical rule presented above, trace (a) has a relative quantum yield of 0.47 while that of trace (b) has diminished to 0.24.

In accordance with the above empirical relationship, we summarize the spectroscopic properties of represented examples of Pc derivatives in the Table below.

Figure 7:
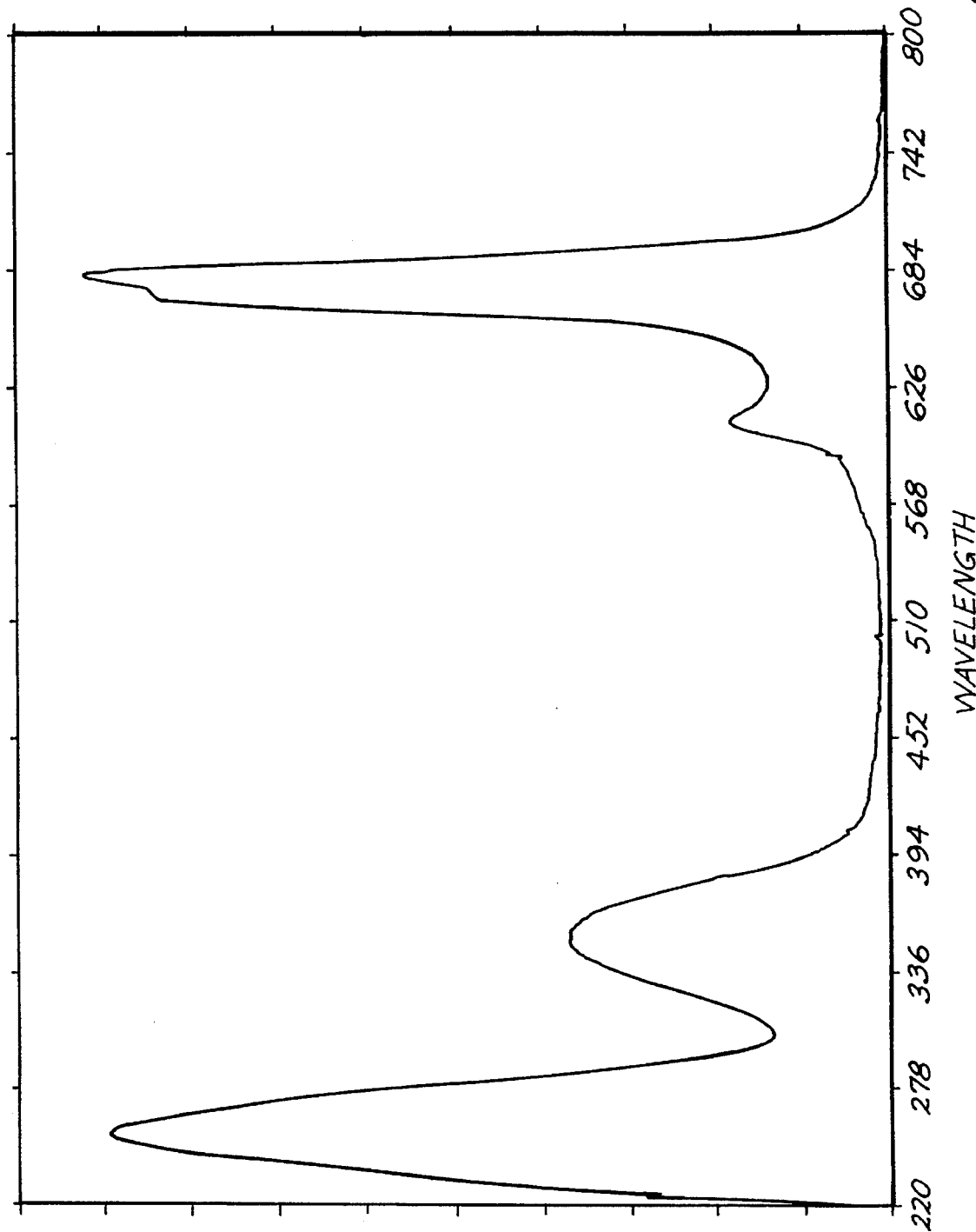
FIG. 7 presents the visible absorption spectra for AlPc-primer prepared as described in Example 3 in 0.1 M triethyl ammonium acetate in water.

| Representative Example | Percent Monomer | $A_{red}/A_{blue}$ | Relative Quantum Yield |
|---|---|---|---|
| AlPcTS (1) Example 1 FIG. 1, trace (a) | 100 | 2.80 | 1.00 |
| AlPc-primer Example 3 FIG. 7 | 100 | 2.48 | 0.80 |
| AlPc-streptavidin conjugates Example 4 | | | |
| A | 78 | 1.73 | 0.25 |
| B | 86 | 2.13 | 0.40 |
| C | 83 | 1.83 | 0.24 |
| D | 91 | 2.23 | 0.47 |
| Hara el al. | | | |

-continued

| Representative Example | Percent Monomer | $A_{red}/A_{blue}$ | Relative Quantum Yield |
|---|---|---|---|
| FePc-HSA[1] | 8.6 | 0.90 | — |
| | <8.6 | 0.65 | — |

[1] The two iron tetracarboxyphthalocyanine conjugates to human serum albumin as described in FIG. 1 of Bull. Chem. Soc. Jpn. 56:2965–2968, 1983. No fluorescence yield is reported. However, even in monomeric form FePc is nonemissive.

Thus, the most preferred embodiments of the phthalocyanine conjugates of the invention, in terms of monomeric binding, have an A(red)/A(blue) ratio $\geq 2$. Such conjugates are readily prepared by Method 3.

Preferably, the A(red)/A(blue) ratio of the subject phthalocyanine conjugates should be $\geq 1.75$, and such conjugates are readily prepared by Method 2.

Phthalocyanine conjugates having A(red)/A(blue) ratios between about 1.5 and 1.75, while suitable for some purposes, have relatively limited sensitivty and so would not be useful, e.g., in the disclosed digoxin assay.

Phthalocyanine conjugates having A(red)/A(blue) ratios of less than 1 are considered to be not suitable for use as fluorescent markers.

A demonstration of the sensitivity inherent in such aluminum phthalocyanine conjugates is presented in Example 5.

Spectroscopic data indicates that aluminum phthalocyanine trisulfonate has a fluorescence emission lifetime of 5 ns and a polarization coefficient of 0.005, from which we conclude that compound 1 is also suitable for a homogeneously based assay using fluorescence polarization changes upon antigen-antibody interaction when the aluminum phthalocyanine trisulfonate is tethered to a small antigen like a drug metabolite.

The maximum quantity of monomeric rather than dimeric or polymeric aluminum phthalocyanine may be coupled to small antigens with the use of a tether linker. Representative protocols for preparation of tether linker modified phthalocyanines and a phthalocyanine labeled small antigen are presented in Examples 2 and 3.

The maximum quantity of monomeric rather than dimeric or polymeric aluminum phthalocyanine may be coupled to large molecules such as antigens, protein carriers or protein carriers functionalized with one or more antigens, enzymes, binding proteins (e.g. streptavidin), or antibodies by one of three methods.

Method 1: In the first method, aluminum phthalocyanine may be coupled to a large molecule with the use of a tether linker. The tether linker may be any small bifunctional organic molecule. The tether linker may be 2 to 12 atoms in length. Preferably, the tether linker is 7 to 12 atoms in length and sterically hindered. A long sterically hindered tether ensures that aluminum phthalocyanine is displaced from the biological entity and that individual aluminum phthalocyanine moieties on the large molecule are displaced from one another. The tether linker method may be utilized in conjunction with Methods 2 and 3.

Method 2: Aluminum phthalocyanine may be coupled to large molecules with the use of an aqueous solvent containing a disaggregated organic such as DMF. Use of the disaggregant helps to ensure that aluminum phthalocyanine is bound in a monomeric rather than aggregated state.

Method 3: In a third method, aluminum phthalocyanine may be coupled to large molecules by preincubation of the fluorophore in a disaggregating medium followed by coupling of the fluorophore to a large molecule in an aqueous solvent containing a disaggregating organic solvent such as DMF. The preincubation is preferably performed by mixing a reactive derivative of aluminum phthalocyanine with dimethylformamide for one hour at 30° C. prior to conjugation in a disaggregating medium. The preincubation of fluorophore in a disaggregating organic solvent (e.g., DMF) prior to conjugation in a disaggregating medium is the first disclosure of such a method for generating monomeric conjugates with any fluorescent species including phthalocyanines and porphyrins.

Representative protocols for each of these coupling methods are presented in Example 4. The preferred method for coupling involves the preincubation of the phthalocyanine in a disaggregating medium for one hour prior to conjugation in a disaggregating medium. In general, Method 3 produces conjugates with a very high degree of monomerism that are highly emissive. For example, an AlPc—streptavidin conjugate prepared via Method 3 has greater than 90% of the phtha ocyanine molecules covalently bound to the streptavidin in monomeric form, as well as an A(red)/A(blue) ratio of 2.23 and a relative quantum yield of 0.47 (see FIG. 8). Furthermore, we have found that the procedure is generally applicable to any large molecular weight species (e.g., antibodies, enzymes, etc.). It is contemplated that a combination of Methods 1 and 3 will yield the most monomeric aluminum phthalocyanine conjugates.

Use of aluminum phthalocyanine for nucleic acid probe assays, whether in solution or on solid matrices (e.g., nitrocellulose), requires the coupling of one or more monomeric phthalocyanines to a nucleic acid primer or probe. The phthalocyanine may be coupled directly to a primer or probe with the use of a tether linker. Alternatively, the probe or primer may be modified with a ligand binder (e.g., biotin) by a method such as nick translation such that a phthalocyanine modified binding partner (e.g., streptavidin) may be bound. Both methods have been demonstrated to yield aluminum phthalocyanine modified primer or probes that retain both emissivity and the ability to hybridize.

Aluminum phthalocyanine may be covalently attached to a DNA sequencing primer, oligonucleotide, nucleic acid probe or dideoxynucleotide for use in automated or manual DNA sequencing. Since detection is accomplished in a matrix (e.g., acrylamide), and the quantity of material to be detected is small, spectral properties indicate that aluminum phthalocyanine based sequencing reagents are superior to those based on fluorescein or rhodamine. The preferred method for attachment of aluminum phthalocyanine for these applications uses a tether linker in a disaggregating medium. Using this method, a trisulfonyl chloride derivative of aluminum phthalocyanine was covalently attached to the 5' end of an amino modified primer. The resultant aluminum phthalocyanine conjugate is completely monomeric, as is evidenced by the absence of the dimer absorbance in the visible spectrum (see FIG. 7) and its very bright emission. This small molecule conjugate has an A(red)/A(blue) ratio of 2.48 and a relative quantum yield of 0.80. These values fall on the line corresponding to the unconjugated dye in FIG. 5. A representative synthetic protocol is disclosed in Example 3. Comparison of the sequencing results of aluminum phthalocyanine modified primer with those obtained for the starting primer reveals that modification of the primer with the phthalocyanine does not significantly alter the ability of the primer to function in a sequencing reaction.

For fluorescence microscopy, imaging, or flow cytometry applications that rely on specific binding, aluminum phthalocyanine must be monomerically coupled to an antigen, antibody or other immunological binding partner, ligand binding carrier (e.g., streptavidin), or probe (e.g., membrane, nucleic acid, etc.). Representative protocols for such couplings and performance data are presented in Example 4. The preferred method for coupling uses preincubation of the phthalocyanine in a disaggregating organic solvent with conjugation in a disaggregating medium. Using the preferred method, aluminum phthalocyanine has been used to label a number of species including streptavidin, antibodies specific for human T cells (e.g., anti-T4 and anti-T8), theophylline monoclonal antibodies, and goat anti-mouse polyclonal antibodies. The resultant conjugates have been used to detect a variety of biological entities including human chromosomes, and human and mouse lymphocytes. The labeled entities have been detected with a flow cytometer (using UV or helium neon laser excitation), a laser scanning confocal microscope (helium neon or diode laser excitation), or a microscope with associated CCD camera and image intensifier. A representative set of data for the use of aluminum phthalocyanine labeled streptavidin for application to flow cytometric human lymphocyte subset analysis is presented in Example 4.

Alternatively, aluminum phthalocyanine may be nonspecifically bound to proteins or nucleic acids by way of an ionic interaction. Thus, positively charged aluminum phthalocyanine derivatives similar to those disclosed in Example 2 may be bound nonspecifically to intra- or extracellular DNA or RNA by way of the negatively charged phosphate residues on the nucleic acids. The preferred phthalocyanine will specifically bind to either DNA or RNA. Moreover, the unbound phthalocyanine will be nonfluorescent until bound to the nucleic acid. Operationally, a phthalocyanine that is aggregated in solution will be nonemissive and will therefore satisfy the first condition for the above application. The second condition is satisfied when the interaction of the phthalocyanine and the nucleic acid results in monomeric binding. The monomerically bound phthalocyanine is highly fluorescent and therefore provides a quantitative measure of either the DNA or RNA present.

Lipophilic derivatives of aluminum phthalocyanine may be used as fluorescent probes of cellular membranes. Hydrophobic substituents (long alkyl chains, for example) on the aluminum phthalocyanine would enable its use in these applications. The lipophilic character of the fluorescent probe may be incorporated as set forth in Examples 2 and 3. Treatment of the reactive phthalocyanine with an amino alkane provides such a probe. The preferred membrane probe is highly fluorescent and is held strongly in the membrane.

The ultimate sensitivity of a fluorogenic enzyme assay is determined by the spectral properties of the generated fluorophore. Water-soluble monomeric aluminum phthalocyanine species display spectral properties superior to currently available fluorophores (e.g., DBDA, MUN, F, R-B). As previously stated, aluminum phthalocyanine trisulfonate has a high quantum efficiency of emission (QY=0.6), a large Stokes shift (335 nm), and an emission wavelength (680 nm) red-shifted from the emissions of endogenous fluorophores. Therefore, the use of an enzyme-substrate couple that enzymatically generates a monomeric aluminum phthalocyanine in the test solution would represent an improvement over the present technology.

One way to use aluminum phthalocyanine as an enzyme substrate would be to convert it to a nonemissive species that becomes emissive upon enzyme cleavage. Fluorescent molecules may be rendered nonemissive (quenched) by covalent attachment to small molecules containing heavy atoms such as iodine. For example, fluorescein isothiocyanate (FITC)

becomes less emissive upon covalent attachment to thyroxine; the iodines bound to the aromatic rings of thyroxine decrease the fluorescence emission of the fluorescein by a factor of ten. Phthalocyanines may be quenched by the presence of heavy atoms. The covalent attachment of an iodine-containing small molecule renders an aluminum phthaloocyanine derivative essentially nonemissive. Representative protocols are set forth in Example 7 for the synthesis of such nonemissive aluminum phthalocyanine enzyme substrates. Once cleaved by the enzyme, the monomeric phthalocyanine is fully emissive in solution. Such reagents can be utilized in conventional enzymatic assays, e.g., immunoassays or cDNA probe assays, and as reporting groups as disclosed in Example 7.

In another aspect, the invention provides chromogenic monomeric phthalocyanine reagents for use in colorimetric immunoassays. For such applications the phthalocyanine 1 is preferably metallated with copper, but other metals (M), notably aluminum or silicon, can be used. Because aggregation reduces the molar absorptivity of the phthalocyanine species, any of the foregoing strategies that decrease aggregation (including but not necessarily the provision of an axial ligand) can be employed to provide a more absorptive species. Example 8 sets forth representative protocols for the preparation of such reagents.

In a further aspect, the invention provides therapeutic monomeric phthalocyanine reagents. For photoimmunotherapy, it is critical that the photosensitive agent retain its photodynamic activity after conjugation to a tumor-directed antibody or other binding fragment. This criterion is satisfied in the case of metallophthalocyanine sensitizers only by ensuring that the phthalocyanine reagents are monomerically coupled to the antibody, for self-quenching of the aggregated species would otherwise impair the generation of singlet oxygen in vivo. Suitable protocols for monomerically binding the phthalocyanine to an antibody are presented in the Examples. Preferred metals (M) for this therapeutic purpose are aluminum, scandium, gallium, and zinc.

The invention is further illustrated by the following representative Examples.

EXAMPLE 1

Preparation of Sulfonated Aluminum Phthalocyanine

There are several reported methods for the synthesis of sulfonated phthalocyanine compounds. As examples, one may treat a phthalocyanine with: fuming sulfuric acid; sulfuric acid monohydrate with 20% oleum; chlorosulfonic acid followed by hydrolysis; or sulfur trioxide-pyridine. Sulfonation of aluminum phthalocyanine (AlPc) with oleum yields a mixture of aluminum phthalocyanine compounds containing predominantly the trisulfonate. Representative synthesis protocols follow.

Chlorosulfonic acid method: In a representative synthesis, 3.0 mL chlorosulfonic acid was added to 396 mg (0.069 mmol) chloro-aluminum phthalocyanine in a 25 mL round bottom flask fitted with a stir bar. The mixture was stirred to effect dissolution, sealed under argon, and immersed in a preequilibrated oil bath at 145° C. The solution was stirred at 145° C. for 2 hours, cooled to 0° C., and quenched by gradual addition to 25 g of ice. The solid contained within the resultant slurry was collected by suction filtration, washed with 100 mL water, 300 mL dichloromethane, and then dried under partial vacuum for several hours. The resultant blue solid was characterized by elemental analysis and found to have a N:S ratio consistent with that anticipated for the aluminum phthalocyanine trisulfonyl chloride. The $^1$H NMR (500 MHz) analysis reveals that the material is a mixture of sulfonated materials. The temperature and time utilized for sulfonation greatly affect the product distribution.

Conversion to aluminum phthalocyanine trisulfonate: To 200 mg of predominantly aluminum phthalocyanine trisulfonyl chloride was added 1.0 mL 1N sodium hydroxide. This mixture was stirred for 24 hours at room temperature, concentrated under vacuum, and purified by preparative thin layer chromatography (1 10% sodium hydroxide: 3 methanol). The resultant blue solid was analyzed by elemental analysis, and found to have a N:S ratio consistent with aluminum phthalocyanine trisulfonate. Analysis by $^1$H NMR reveals that this material is a mixture of sulfonated materials. A representative visible absorption spectrum is shown in FIG. 1 (trace a). This species is 100% monomeric.

The sulfonations of aluminum phthalocyanine described above result in mixtures of phthalocyanines, in which the average number of sulfonate groups per phthalocyanine is three.

Metallation of free base phthalocyanine tetrasulfonate: Free base phthalocyanines, as with the porphyrins, can be metallated with a variety of species to yield the corresponding metallo analogs. Metallation may be effected with a variety of reactive metal sources including trialkyl, preferably trimethyl, metal and metal trichloride. For example, free base tetraphenylporphine has been metallated with trimethyl aluminum to yield the corresponding aluminum derivative. To date, the metallation of a sulfonated free base phthalocyanine with a reactive derivative of aluminum has not been reported. Thus, the following novel syntheses are presented.

Trimethyl aluminum method: To a dry 10 mL round bottom flask fitted with stir bar was added 50 mg (0.06 mmol) free base phthalocyanine tetrasulfonate (Porphyrin Products, Logan, Utah). The flask was sealed under argon, and the contents were diluted with 1.0 mL dimethylformamide (DMF). After stirring 10 minutes at room temperature to effect dissolution, the solution was treated with 0.7 mL (1.3 mmol) trimethyl aluminum (1M in toluene), stirred at 25° C. for 12 h, and concentrated under vacuum. Extraction with methanol followed by concentration of the methanolic solution under vacuum led to the isolation of 5 mg aluminum phthalocyanine.

Triacetonylacetonate aluminum method: To 100 mg (0.12 mm) phthalocyanine tetrasulfonate (Porphyrin Products, Logan, Utah) in 5.0 mL DMF was added 10 equivalents, 390 mg (1.2 mm) triacetonylacetonate aluminum. After stirring for 2 hr at room temperature, metallation was complete as judged by the visible absorbance spectrum. The solution was diluted with 100 mL methylene chloride to precipitate the reaction product. The product was isolated by filtration, washed with 200 mL methylene chloride and dried. Aluminum acetonylacetonate phthalocyanine tetrasulfonate was isolated as a blue powder, 106 mg, 92%.

Metallophthalocyanines may also be prepared by the dilithium phthalocyanine method.

Dilithium phthalocyanine method: Treatment of dilithium phthalocyanine (prepared by reaction of phthalonitrile with a lithium alkoxide in alcohol) with metallo acetylacetonates or chlorides produces the corresponding metallophthalocyanine in good yield. A representative synthesis is as follows. To 500 mg (3.90 mm) phthalonitrile in 5 mL 4-methyl-1- butanol at 140° C. was added a solution of 100 mg (14.3 mm) lithium in 5 mL 4-methyl-1-butanol. After reflux under inert nitrogen atmosphere for 2 hours, the mixture was treated with either 356 mg (1.1 mm) aluminum acetylacetonate or 256 mg (1.1 mm) aluminum trichloride hexahydrate and refluxed for an additional 2 hours. The crude reaction mixture was concentrated under vacuum and then diluted with 50 mL methylene chloride. The product is precipitated from methylene chloride by the addition of 100 mL methanol, collected by filtration, and washed with an additional 100 mL methanol. Obtained as blue-green powders were 208 mg, 33%, aluminum acetonyl phthalocyanine, or 338 mg, 58%, aluminum chloride phthalocyanine, respectively. Other metals incorporated by this method include Zn, Ga, Sc, Si, and Ge.

Total synthesis: Metallophthalocyanines can be prepared by reaction of: phthalonitriles with metal salts (phthalonitrile process); phthalic acid derivatives with urea and metal salts (urea process); or diiminoisoindoline derivatives with metal salts. See: The Phthalocyanines, Volume 2, F. H. Moser and A. L. Thomas, CRC Press, Boca Raton, Fla., 1983. A total synthesis of true tetrasulfonated aluminum phthalocyanine has not been reported. The urea method is described in Weber, J. H. and D. H. Busch, *Inorg. Chem.* 4:469, 1965; Bauman, F., U.S. Pat. No. 2,613,128; and Fukada, N., *Nippon Kagaku Zasshi*, 75:1141, 1954. The products of such reactions are necessarily a mixture of the four isomers of tetrasulfonated aluminum phthalocyanine. Exemplary total syntheses of aluminum phthalocyanine tetrasulfonate follow:

Synthesis via melt: A finely ground mixture of 133 mg (1.0 mm) aluminum trichloride, 1.25 g (4.0 mm) 4-sulfophthalic acid trisodium salt, 1.20 g (20 mm) urea, 107 mg (2.0 mm) ammonium chloride, and 15 mg (0.012 m m) ammonium molybdate was heated at 280° C. under nitrogen for 2.5 hours. After cooling, the crude product was extracted with 50 ml methanol and concentrated. The product was taken up in 20 ml distilled water and dialyzed exhaustively against distilled water (3,500 MW cutoff dialysis tubing). The aluminum phthalocyanine tetrasulfonate was produced in about 10% yield and was characterized by 1H NMR, UV/Vis absorbance, and fluorescence spectroscopies.

Synthesis via solution: Heating a solution of the above reactants in 10 ml nitrobenzene at 180° C. for 4 hours under nitrogen also produced aluminum phthalocyanine tetrasulfonate in approximately the same yield. Nitrobenzene was decanted from the crude reaction mixture and the residue was washed with benzene to remove the remaining traces of nitrobenzene. The solid was taken up in distilled water and purified by dialysis as above.

The starting material for the above preparations is sulfophthalic acid which is commercially available for Aldrich Chemical Company as the trisodium salt and from Tokyo Chemical Industry Company (TCI) as the triammonium salt. Both products are a mixture of 3-sulfo and 4-sulfophthalic acid. The Aldrich material is a 3:1 mixture with 4-sulfo predominating; TCI's product is approximately 1:1. The number of isomeric tetrasulfonated phthalocyanines produced from these starting materials is therefore greater than four.

EXAMPLE 2

Preparation of Reactive Aluminum Phthalocyanine

Representative synthesis protocols for tethering sulfonated analogs of aluminum phthalocyanine are disclosed below.

Direct attachment via reactive sulfonic acid derivative: A reactive aluminum phthalocyanine sulfonic acid derivative can be covalently attached directly to any physiological analyte (A) that contains a reactive nucleophile (e.g., A—$NH_2$, A—OH, A—SH, etc.) For example, any amino compound can be coupled to aluminum phthalocyanine trisulfonyl chloride. The following representative protocol describes such a coupling to p-amino benzoic acid (PABA). To a stirred solution of 42 mg (0.4 mmol) $Na_2CO_3$ in 1.0 mL $H_2O$ at 80° C. was added 27 mg (0.2 mmol) PABA. After stirring 5 minutes at 80° C., 100 mg (0.1 mmol) aluminum phthalocyanine trisulfonyl chloride was added gradually with stirring. After 12 hours at 80° C., the mixture was cooled to 25° C. and then concentrated under vacuum. The resultant blue solid was subjected to exhaustive acetone trituration to yield the corresponding mono-PABA-sulfonamide. In a preferred synthetic protocol, the aluminum phhaloeyanine PABA sulfonamide may be prepared by treatment of aluminum phthaloeyanine trisulfonyl chloride in DMF with 4-aminobenzoic acid in the presence of triethylamine at room temperature.

Alternatively, reagent moieties can be coupled to a water-soluble aluminum phthalocyanine derivative by activation of the sulfonic acid residues, as in the following protocol for attaching PABA to aluminum phthalocyanine trisulfonate. To a 10 mL round bottom flask containing a stirred solution of 150 mg (0.17 mmol) aluminum phthalocyanine trisulfonate in 2.0 mL benzene at 25° C. was added dropwise 0.75 mL (8.6 mmol) oxalyl chloride. After 6 hours at room temperature, the solvent was evaporated in vacuo to yield aluminum phthalocyanine trisulfonyl chloride as a dark blue solid. To a stirred solution of 61 mg (0.58 mmol) of $Na_2CO_3$ in 1.0 mL $H_2O$ at 80° C., was added 31 mg (0.23 mmol) PABA. After 5 minutes at 80° C., 55 mg (0.06 mmol) of the aluminum phthalocyanine trisulfonyl chloride was added. The mixture was stirred at 80° C. for 6 hours, and the solvent was removed by concentration under vacuum. The contents of the flask were diluted with 10% $NH_4OH$ in methanol, reconcentrated under vacuum, and then exhaustively triturated with acetone to give mono-PABA-sulfonyl aluminum phthalocyanine disulfonate.

Attachment of analytes via an amino aluminum phthalocyanine derivative: Sulfonated aluminum phthalocyanine can be converted to amino derivatives by reaction of the corresponding sulfonyl chloride with a diamino compound. For example, to a solution of 24 mg $Na_2CO_3$ in 1.0 mL $H_2O$ at 80° C. was added 15 mg 2,2'-oxybis(ethylamine)hydrochloride. After 5 minutes at 80° C., 50 mg aluminum phthalocyanine sulfonyl chloride was added, the mixture was diluted with an additional 0.5 mL of $H_2O$, and heated at 80° C. for 12 hours to yield the corresponding monoamino derivative.

Attachment of analytes via carboxy aluminum phthalocyanine derivative: Activation of a sulfonated aluminum phthalocyanine followed by treatment with an amino acid yields a mono-, di-, tri- or tetra-carboxy functionalized sulfonated aluminum phthalocyanine. The resultant species is activated to a mixed anhydride by treatment with ethyl chloroformate in triethylamine and dimethylformamide, or coupled directly to reactive nucleophiles (A—$NH_2$, etc.) on the analyte. An exemplary synthesis is presented in Example 3.

EXAMPLE 3

Preparation of Aluminum Phthalocyanine-Small Molecule Conjugates

Aluminum phthalocyanine may be coupled to small molecule antigens or oligonucleotides. Reaction of amino functionalized small molecules with either an activated carboxy or sulfonylchloride derivative of aluminum phthalocyanine in a disaggregating medium gives monomeric phthalocyanine derivatives.

Preparation of aluminum phthalocyanine-morphine conjugate: To a stirred solution of 50 mg $(PABA)_1$—$(SO_2)$—$AlPc$–$(SO_2Cl)_2$ in 0.5 mL triethylamine at 0° C. was added 7 µL ethylchloroformate. After 5 minutes at 0° C., 29 mg 3-(4-aminobutyl)morphine was added; the reaction mixture was warmed to room temperature and stirred for 8 hours to yield the corresponding monomorphine functionalized derivative.

The aluminum phthalocyanine-morphine conjugate described above was evaluated spectroscopically by UV-VIS and fluorescence techniques. These data indicate that the conjugated morphine analog has a relative quantum yield of 0.76, and that direct monomeric conjugation of the aluminum phthalocyanine molecule to a small hapten has very little influence on the emission yield.

The relative immunoaffinity of morphine, the amino morphine analog, and the amino-morphine derivative of mono-PABA-sulfonyl aluminum phthalocyanine disulfonate was determined in a competition experiment with antimorphine monoclonal antibody and tritium-labeled morphine. The relative affinity of the antibody for each of these species is shown in the following table.

| Competitor | Relative Affinity |
| --- | --- |
| morphine | 1 |
| amino morphine | 1 |
| aluminum phthalocyanine-morphine | ~1 |

These results indicate that functionalization of morphine to yield a tetherable analog does not disrupt antibody recognition, and that attachment of approximately one morphine analog to an aluminum phthalocyanine derivative yields a species that is as competitive as the parent compound in an immunoassay.

Preparation of aluminum phthalocyanine-primer conjugate: To a stirred solution of 0.02 µmol amino hexane modified M13mp18 (−21) Universal sequencing primer in 40 µL 0.5M aqueous $NaHCO_3/Na_2CO_3$ (pH adjusted to 9.0) was added 0.9 mg $AlPc$—$(SO_2Cl)_3$ in 12 µL DMF. After stirring for one hour in the dark, the aluminum phthalocyanine labeled primer was purified by ethanol precipitation followed by polyacrylamide gel electrophoresis. The aluminum phthalocyanine-primer conjugate was evaluated by UV-Vis absorption and fluorescence spectroscopies. FIG. 7 shows the visible absorbance spectrum of AlPc-primer. The UV-Vis data indicated a 1:1 ratio between primer and phthalocyanine. Comparison of the fluorescence emission of the primer conjugate with that of aluminum phthalocyanine trisulfonate revealed it to be 80% as emissive as the parent species, with an A(red)/A(blue) ratio of 2.48. The aluminum phthalocyanine in the AlPc-primer is 100% monomeric. UV excitation of the aluminum phthalocyanine labeled primer in an acrylamide matrix showed it to be emissive with a signal-to-background ratio 50-fold higher than that observed for fluorescein. The functional activity of the Universal sequencing primer was unaltered as a result of derivatization with aluminum phthalocyanine. A Sanger dideoxy chain terminating sequencing reaction was performed with deoxynucleotides, $^{32}P$-cytidine triphosphate, TAQ polymerase, template DNA, each of the dideoxynucleotides, and either unmodified or aluminum phthalocyanine modified primer. Aside from slight differences in the electrophoretic mobility of the sequencing fragments, the sequencing results were identical. Thus, aluminum phthalocyanine labeled primers may be utilized for either manual or automated fluorescence based DNA sequencing.

EXAMPLE 4

Preparation of Aluminum Phthalocyanine-Large Molecule Conjugates: Application to Flow Cytometry and Fluorescence Microscopy Direct conjugation of aluminum phthalocyanine to a protein molecule such as bovine serum albumin (BSA) or avidin was found to yield a protein conjugate with unexpectedly low emissivity. As a result, we have determined that the most highly emissive aluminum phthalocyanine protein conjugates will result from indirect coupling with the use of an intermediate tether, direct or indirect coupling in a disaggregating medium, and/or direct or indirect coupling of a reactive aluminum phthalocyanine derivative that has been disaggregated by incubation in a disaggregating medium.

Indirect coupling with an intermediate tether: In the indirect tether method, the linking tether should be at least two and preferably from about four to twelve atoms in length. Longer tethers are preferred when interaction of the phthalocyanine with the biological entity is undesirable, as they ensure a maximum distance between the phthalocyanine and the biological entity of interest. Furthermore, linking tethers with greater steric hindrance yield more monomeric products. Synthetic protocols employing two different types of tethers are outlined below. Sterically hindered or bulky tethers attached to aluminum phthalocyanine make it impossible for two phthalocyanine moieties attached to a biological entity of interest to come close enough to aggregate. Thus monomeric rather than dimeric or polymeric aluminum phthalocyanine is attached to the entity of interest.

In a first protocol, treatment of aluminum phthalocyanine (AlPc) with chlorosulfonic acid followed by aqueous quench and isolation leads to the formation of aluminum phthalocyanine trisulfonyl chloride. Reaction of the trisulfonyl derivative and any of a variety of amino acids in an organic solvent yields a carboxylic acid functionalized derivative. In addition to 4-aminobenzoic acid, we examined trans-4-(aminomethyl)cyclohexane carboxylic acid, glycine, and 8-amino-3,6-dioxyoctanoic acid as indirect linkers. Of these four amino acids, the largest and most sterically hindered, trans-4-(aminomethyl)-cyclohexane carboxylic acid, yielded the most monomeric and most highly emissive aluminum phthalocyanine adduct. Activation of the carboxylic acid functionality followed by direct coupling of the activated derivative to the amino groups of either streptavidin or an antibody in a dissociating solution containing less than twenty percent organic solvents yields the desired monomeric aluminum phthalocyanine-protein conjugate.

In a second synthetic protocol, treatment of aluminum phthalocyanine trisulfonyl chloride with any of a number of diamines leads to the formation of an amino derivative. Coupling of succinimidyl-4-(N-maleimidomethyl) cyclohexane 1-carboxylate (SMCC) to the amino derivative yields the corresponding maleimide. A separate reaction of the amino groups of either an antibody or streptavidin with S-acetylmercaptosuccinic anhydride in sodium phosphate buffer, followed by quenching and Sephadex purification, yields a thiolated species. Conjugation of the thiolated protein with the maleimide derivative in the dissociating solution gives the desired monomeric aluminum phthalocyanine-protein conjugate.

Direct coupling in a disaggregating medium: To 4.4 mg AlPc—(SO$_2$Cl)$_3$ solid was added 400 μL of dry dimethylformamide (DMF). The AlPc—(SO$_2$Cl)$_3$ was dissolved and 6.0 μL of the solution was immediately added dropwise to 0.45 mg streptavidin in 80 μL of 0.2M sodium bicarbonate (NaHCO$_3$) in phosphate buffered saline (PBS) pH adjusted to 9.0 containing 14.0 μL DMF at 4° C. After 30 minutes, the reaction was diluted with 0.5 mL 0.2M NaHCO$_3$ in PBS containing 0.02% sodium azide as a preservative. The conjugate was purified by exhaustive dialysis followed by size exclusion chromatography (Sephadex G-25).

Figure 8:
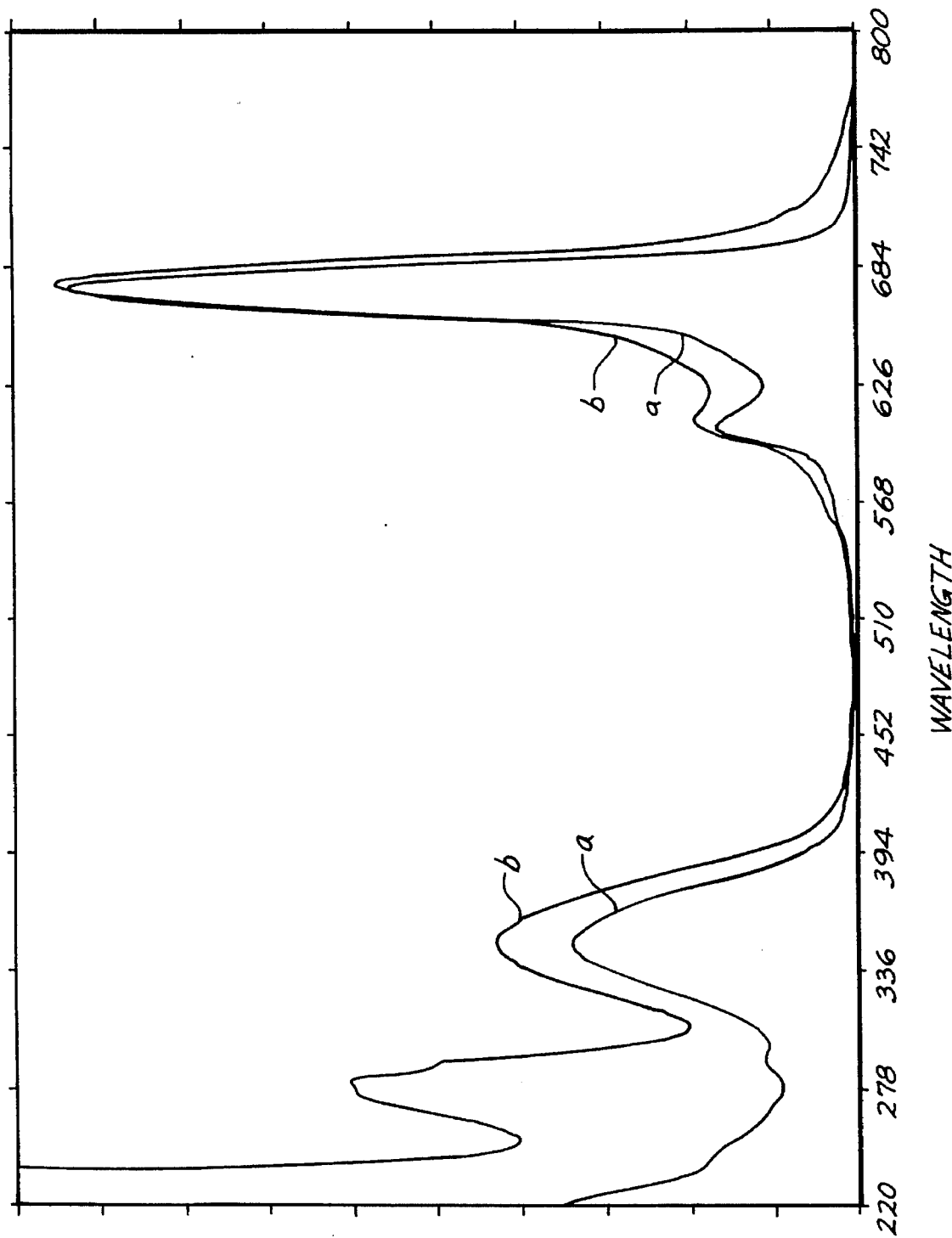
FIG. 8 presents the visible absorption spectra of aluminum phthalocyanine trisulfonate (plot a) as compared to a streptavidin conjugate prepared via Method 3 (plot b) in phosphate buffered saline.

Preparation of improved aluminum phthaloeyanine conjugates by disaggregation of the reactive aluminum phthalocyanine derivative prior to conjugation in disaggregating medium: An improved method for the attachment of monomeric (or disaggregated) aluminum phthalocyanine trisulfonylchloride (AlPc—(SO$_2$Cl)$_3$) to a representative protein (streptavidin) is disclosed below. A comparison of the visible absorbance spectra of AlPc-streptavidin and AlPc trisulfonate is shown in FIG. 8. With the use of Method 3, greater than 90% of the aluminum phthalocyanine is conjugated in monomeric form, with an A(red)/A(blue) ratio of 2.23 and a relative quantum yield of 0.47. To 15.0 mg AlPc—(SO$_2$Cl)$_3$ solid was added 300 μL of dry dimethylformamide (DMF). The AlPc—(SO$_2$Cl)$_3$ was dissolved and the mixture was immersed in a pre-equilibrated dry bath (30° C.) for one hour. After one hour at 30° C., 325 μL of the AlPc—(SO$_2$Cl)$_3$ solution was added dropwise to 15.0 mg of streptavidin in 2.4 mL of 0.2M sodium bicarbonate (NaHCO$_3$) in phosphate buffered saline (PBS) pH adjusted to 9.0 containing 0.275 μL DMF at 4° C. After 30 minutes, the reaction was diluted with 1.0 mL 0.2M NaHCO$_3$ in PBS containing 0.02% sodium azide as a preservative. The conjugate was purified by exhaustive dialysis followed by size exclusion chromatography (Sephadex G-25).

The benefits of conjugation in a disaggregating medium and preincubation of the phthalocyanine in a disaggregating medium prior to conjugation are best illustrated by comparison of the emissivity of similar aluminum phthalocyanine-streptavidin conjugates resulting from coupling under two different sets of experimental conditions. In the first set of experiments, streptavidin was labeled with aluminum phthalocyanine under solely aqueous (sample A) or with the preferred method (Method 3) of preincubation and disaggregation (sample B) to yield conjugates with identical aluminum phthalocyanine loadings (AlPc/Prot.). The relative emissivity (Rel.Em.) of the two conjugates was measured in solution with a Perkin-Elmer MPF66 spectrofluorometer. The two conjugates were then utilized to label human peripheral blood lymphocytes using the method outlined in the following section entitled "Application to flow cytometry". The cells were analyzed with a flow cytometer and the logarithmic fluorescence output (Chann. Sep.) of the AlPc-streptavidin labeled cells was determined. The logarithmic fluorescence output is expressed as channel separation (Chann. Sep.). As can be seen by examination of the results presented in the Table below, coupling of aluminum phthalocyanine to streptavidin using Method 3 yields a conjugate with greater emissivity (100% vs. 50%) that translates to more brightly labeled cells (74 vs. 61) in a practical application. In fact, a channel separation difference of 13 means that the cells labeled with a conjugate prepared by Method 3 are 1.4 times as bright as those labeled with a conjugate prepared under solely aqueous conditions.

| Sample | Medium | AlPc/Prot. | Rel. Em. | Chann. Sep. |
|---|---|---|---|---|
| A | Aqueous only | 2.3 | 50 | 61 |
| B | Method 3 | 2.3 | 100 | 74 |

In the second set of experiments, streptavidin was labeled with aluminum phthalocyanine with the use of a disaggregating medium (Method 2; sample C) or with the preferred method of preincubation and disaggregation (Method 3; sample D) to yield conjugates with identical aluminum phthalocyanine loadings (AlPc/Prot.). The resultant conjugates were evaluated spectroscopically and flow cytometrically as described above. A summary of the data is presented in the Table below.

| Sample | Medium | AlPc/Prot. | Rel. Em. | Chann. Sep. |
|---|---|---|---|---|
| C | Method 2 | 2.8 | 63 | 65 |
| D | Method 3 | 2.8 | 100 | 74 |

As shown in the results, Method 3 yields a conjugate with a greater emissivity (100 vs. 63) than the conjugate obtained by Method 2. The channel separation for cells labeled with the conjugate prepared by Method 3 was greater than that for cells labeled with a conjugate prepared using Method 2 (74 vs. 65). Practically speaking, a Method 3 conjugate yields labeled cells that are 1.3 times brighter than those labeled by Method 2. In sum, conjugates prepared by Method 3 have a higher percentage of monomeric phthalocyanine than those prepared by Method 2 or under solely aqueous conditions.

Application to flow cytometry: Human hymphocyte subset analysis is a typical flow cytometric application of aluminum phthalocyanine. A representative protocol for labeling the T helper cell (anti-CD4 positive) subset of human peripheral blood lymphocytes is as follows. A ficoll-hypaque separation was made on heparinized whole blood to harvest the peripheral blood lymphocytes (PBL). The lymphocytes were washed three times and resuspended in 5% fetal calf serum in phosphate buffered saline (FCS/PBS) at a density of 2.0×10$^7$ cells/ml. To a separate 1.5 ml microcentrifuge tube was added 50 μL (10$^6$ cells) of the parent PBL solution and 20 μL of a biotinylated anti-CD4 antibody at 1×10$^{-7}$ M. This solution was incubated at 4° C. for 15 minutes, and washed once with 1 ml of the FCS/PBS. To the pellet was added 100 μL of a 1×10$^{-7}$ M AlPc-streptavidin conjugate which had been prepared in the disaggregating medium with preincubation. The solution was again allowed to incubate for 15 minutes at 4° C. and then washed two times with FCS/PBS and resuspended in 1 ml of FCS/PBS.

Figure 9:
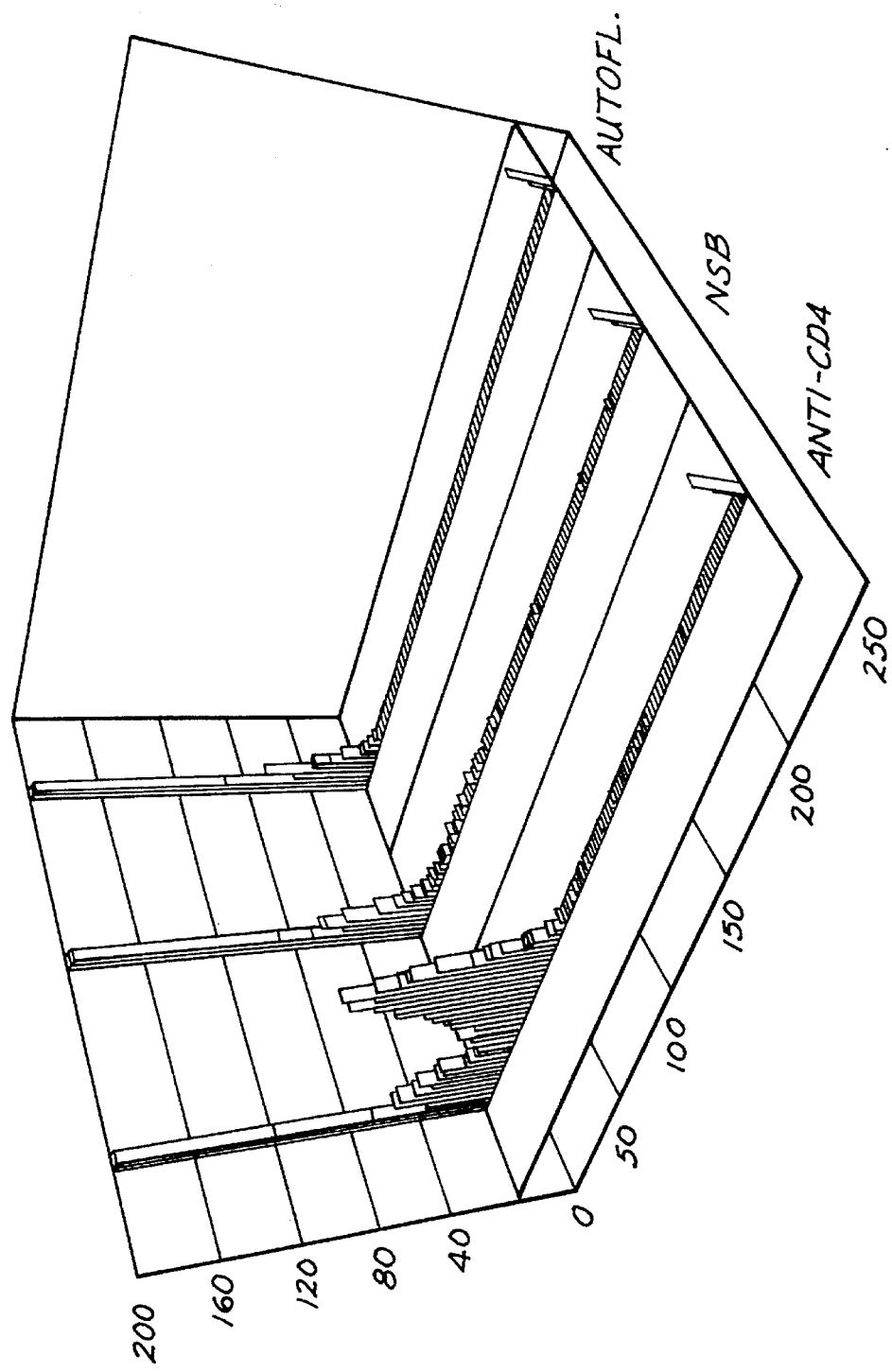
FIG. 9 presents a three-dimensional plot of the flow cytometric data for the T helper cell subset of human peripheral blood lymphocytes as described in Example 4.

Controls for both nonspecific binding (NSB) and cellular autofluorescence (Autofl.) were also prepared as described above. In the case of the autofluorescence reference no biotinylated anti-CD4 or AlPc-streptavidin was added. For the NSB reference the first incubation was performed with an anti-CD4 which was not biotinylated. These samples were read on an EPICS 752 (Coulter Inc.) which was equipped with a helium-neon laser. A three dimensional representation of the data is presented in FIG. 9. The vertical axis of the cytograph presented in FIG. 9 shows cell number. The axis labeled 0, 50, 100, 150, 200, and 250 shows logarithmic fluorescence of the cells. Results show that the anti-CD4 positive cells (Biotinylated CD4 + AlPc-streptavidin) are relatively fluorescent, while the anti-CD4 negative cells (NSB and Autofl.) are not. That is, the population of human lymphocytes that are helper cells (anti-CD4 positive) may be resolved from other types of lymphocytes. Computer quantitation of the amount of anti-CD4 positive cells in the population of lymphocytes reveals that 49% of the lymphocytes are anti-CD4 positive (helper cells). This is the anticipated result. In a normal individual, 50% (±10%) of the lymphocytes should be anti-CD4 positive or helper cells.

EXAMPLE 5

Competitive Fluorescence Immunoassay for Digoxin in Serum

An analyte conjugate similar to those described in Example 8 was prepared for use in a competitive digoxin fluorescence immunoassay (FIA). Streptavidin was labeled with AlPc in a disaggregating medium with preincubation. This protein complex was labeled with digoxin both via covalent chemistries and through the use of the avidin-biotin couple. In the later case digoxin and biotin were covalently attached via a tether linker, and the resulting purified species was added stoichiometrically to the AlPc-streptavidin to assemble the final analyte conjugate. These materials were used as fluorescence tracers in a competitive FIA for digoxin.

The assay procedure involved the addition of 50 μL of serum containing digoxin to 225 μL of a PBS solution which contained a monoclonal anti-digoxin antibody. This solution was incubated in a microfuge tube for 30 minutes at room temperature to establish equilibrium. After this, 50 μL of a 25% suspension of a goat anti-mouse agarose solid capture phase (Sigma, 50–150 μm diameter) was added to the solution. The mixture was incubated at room temperature with shaking for 30 minutes and then washed three times with PBS. After the last wash, 500 μL of a 1N NaOH solution as added to release the bound tracer from the bead. Fluorescence intensity was measured on a Perkin-Elmer MPF 66 fluorometer. As with other competitive assays the signal strength was inversely proportional to the digoxin concentration of the serum sample.

Figure 10:
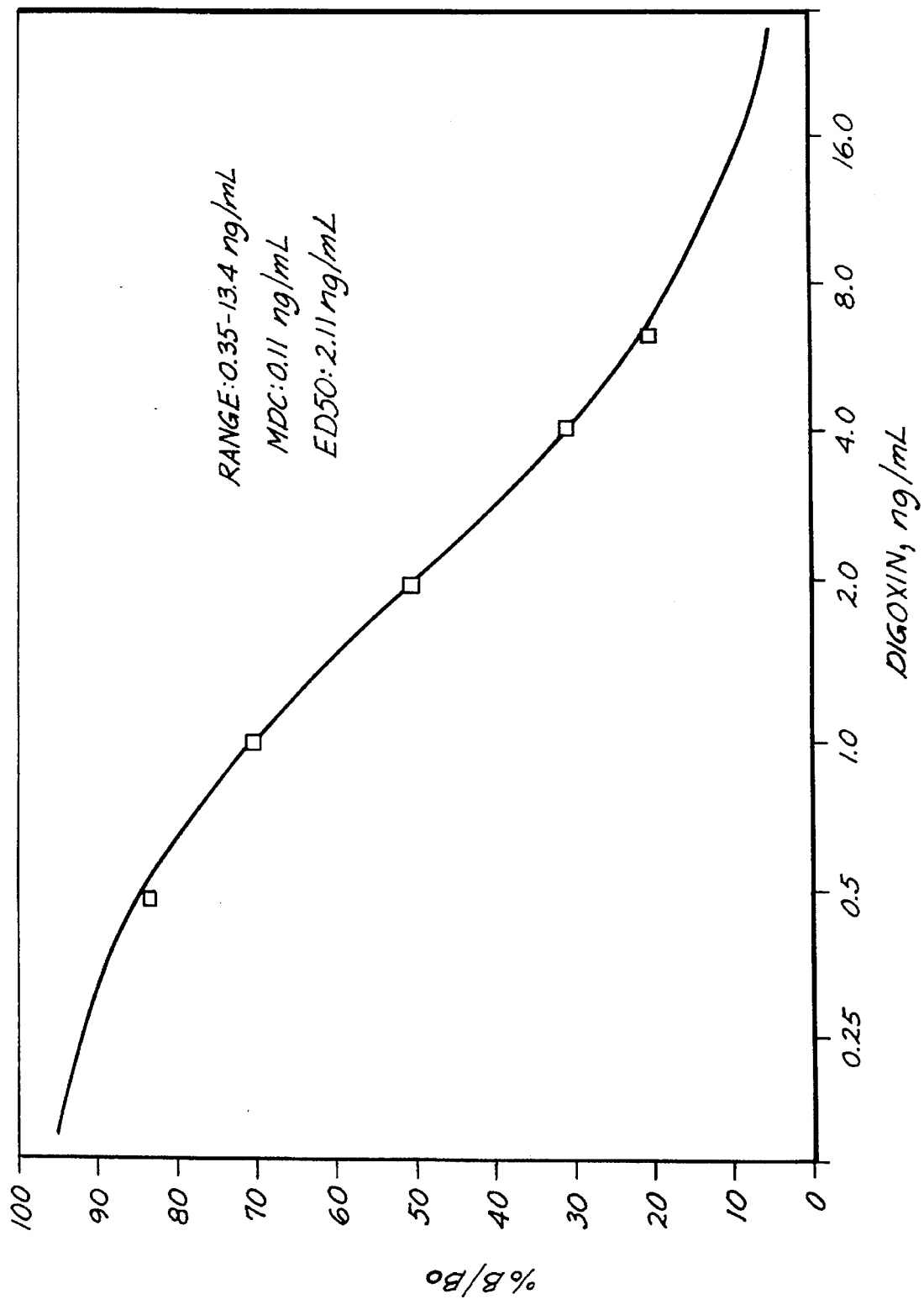
FIG. 10 presents a typical dose response curve for the competitive fluorescence immunoassay for digoxin as described in Example 5.

In FIG. 10 we present the dose response curve for the competitive digoxin FIA described above. The Y axis shows %B/Bo. The %B/Bo is a measure of how much binding out of a theoretical maximum is measured for a given dose of digoxin. Dose of digoxin (x-axis) is the amount of digoxin in ng/ml contained in a given example. Assay precision, clinical range, and minimum detectable concentration were all very acceptable. In addition, this is the only fluorescence based assay for digoxin to date that requires only 50 μL of sample and furthermore does not require protein precipitation or removal to eliminate spectral interferences.

EXAMPLE 6

Preparation of Dyed Microspheres

Dyed microspheres can be prepared by the incorporation of free base or metallated phthalocyanines in the polymeric beads. These beads can then be used as detectable markers in immunoassays, nucleic acid probe assays, hybridization assays, flow cytometry and microscopy. For optimum dye incorporation, the phthalocyanine should be soluble in an organic solvent and insoluble in water. One method used to dye microspheres employs a two-phase system. Here the microspheres are first suspended in water free of surfactant. An appropriate organic solution containing the phthalocyanine dye where the dye is at least 90% monomeric is then added slowly with stirring. The organic phase must be capable of swelling the microsphere to allow the dye to diffuse inside the polymer matrix, but should not be miscible in water. The volume of organic should not exceed that which can be absorbed by the microspheres. Examples of such organics when dyeing polystyrene microspheres with aluminum phthalocyanine chloride are chloroform or cyclohexanone which contain 20% ethanol by volume. After the addition is complete, the solution is allowed to equilibrate for about one day and then the organic is removed by evaporation. The beads are washed several times with water containing surfactant to remove excess dye and then resuspended in aqueous solution containing either surfactant or protein. These beads are suitable as calibrators and standards for flow cytometry. A ligand or ligand-binding patter can be either adsorbed or covalently attached to the surface of these microspheres. Beads prepared in this manner are usable in the assay systems described above.

EXAMPLE 7

Preparation of Reversibly Nonemissive Aluminum Phthalocyanine Reagents

An improved fluorogenic assay is configured as a heterogeneous competitive enzyme assay in which the analyte and an analyte-enzyme conjugate are incubated with an analyte-specific antibody that recognizes both the analyte and the analyte-enzyme conjugate. Competition ensues for binding sites on the antibody. As the amount of analyte present in the test solution increases, the amount of analyte-enzyme conjugate bound to the antibody decreases. After an incubation period, the antibody-bound analyte and analyte-enzyme conjugate reagents are removed from solution, for example, by adding solid-phase immobilized antibody directed against the analyte-specific antibody. The antibody-bound analytes and analyte-enzyme conjugates are thereby immobilized on the solid phase, which is then washed to remove all traces of free analyte and analyte-enzyme conjugate. Thereafter, the solid phase is incubated with a nonemissive aluminum phthalocyanine conjugate that can be enzymatically cleaved to yield a highly emissive monomeric aluminum phthalocyanine derivative in the test solution. If the solid phase contains analyte-enzyme conjugate, monomeric phthalocyanine derivative will be generated and the resultant fluorescence signal will be indirectly proportional to the amount of analyte that was present in the test solution.

The none missive aluminum phthalocyanine derivative that becomes emissive upon enzyme cleavage can be configured in several ways that take advantage of the heavy atom effect, dimerization (self-quenching), or charge transfer.

Heavy atoms such as iodine are known to quench the fluorescence emission of phthalocyanines. Thus, the reagent conjugate for this assay can take the form of an aluminum phthalocyanine derivative with an iodine atom covalently attached via an enzyme-cleavable linkage. The iodine atom may be so linked to the aluminum phthalocyanine derivative at the axial position (L) or to the macrocycle or substituents (R) thereon. Since horseradish peroxidase is known to cleave aromatic and aliphatic iodides, representative species 2–4 (wherein "-CH$_2$I" here indicates any tether that bears an alkyl or acyl iodide) can function as horseradish peroxidase substrates.

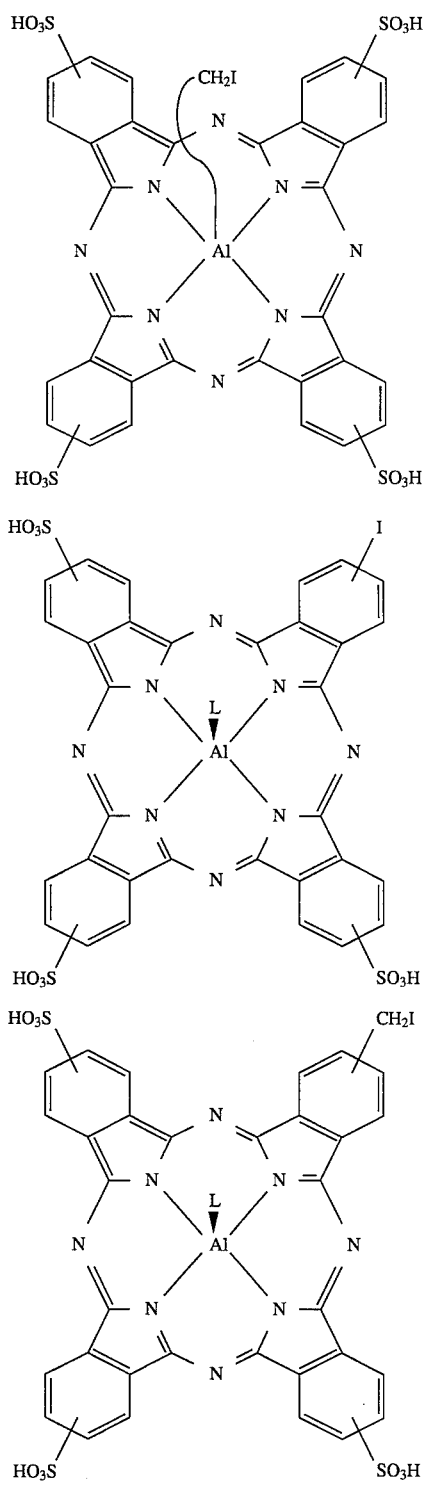

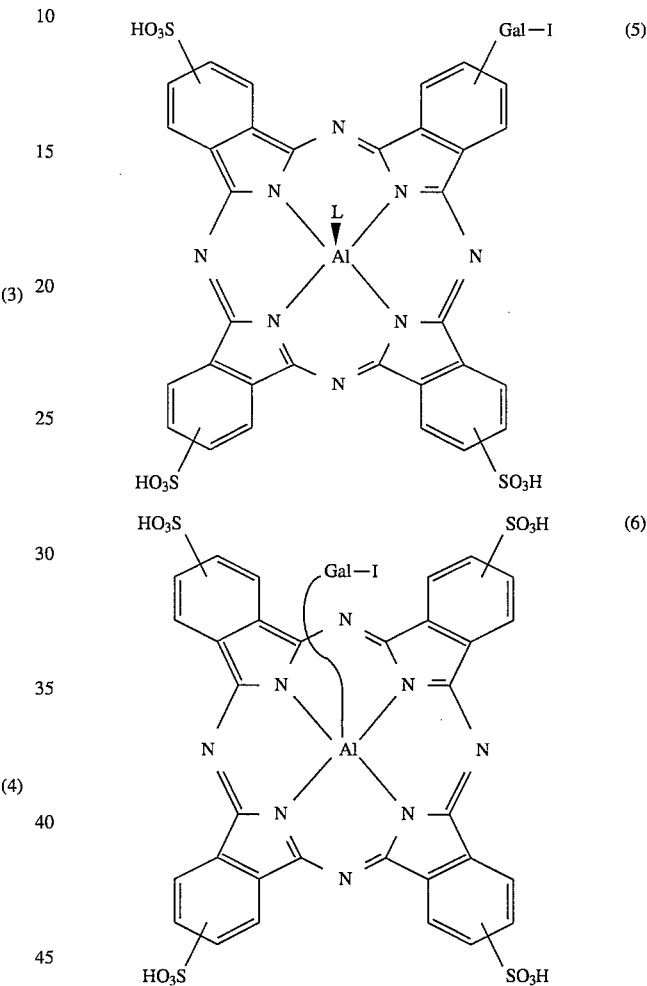

Alternately, the heavy metal atom or a paramagnetic species (e.g., a copper or iron atom, a nitroxide, or other spin label) is attached to the aluminum phthalocyanine derivative by any of a number of enzyme cleavable linkages. For example, attachment of the iodine via a galactose residue, as illustrated in representative species 5 and 6, yields a β-galactosidase enzyme substrate.

Covalent dimers of aluminum phthalocyanine may alternatively be generated by axial ligation or macrocycle dimerization. Three exemplary embodiments 7, 8a, and 8b are illustrated, in which enzyme-clearable linkage(s) (Ec) serve to reversibly bind the monomers to one another.

(7)

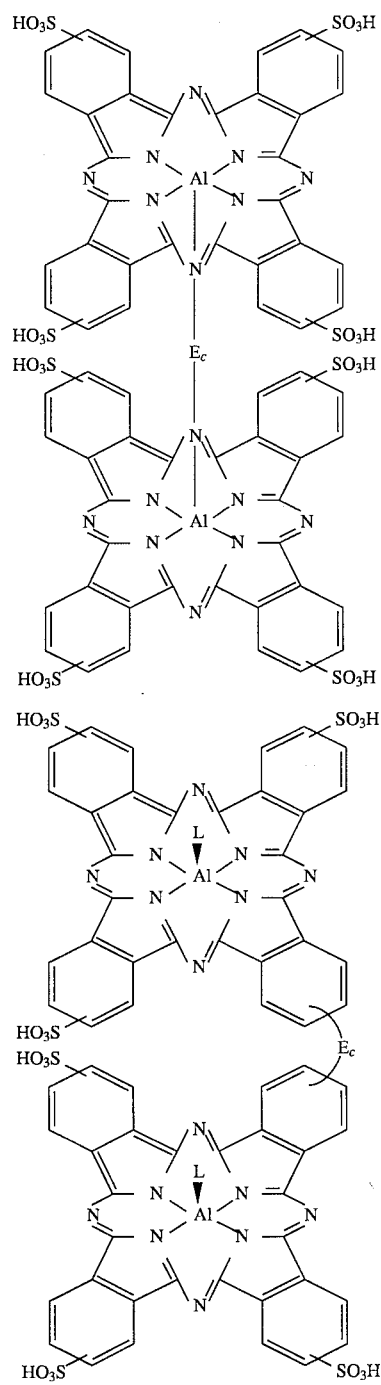

(8a)

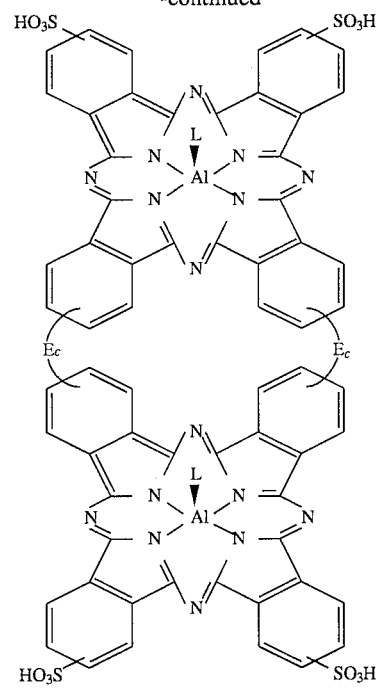

(8b)

For example, the two species may be joined by a galactose moiety thus providing a β-galactosidase substrate.

EXAMPLE 8

Chromogenic Monomeric Phthalocyanine Reagents

The following Example discloses representative chromogenic analyte conjugates for use in immunoassays, and protocols for their preparation. These representative analyte conjugates employ bovine serum albumin (BSA) as a macromolecular carrier. To the BSA core are attached monomeric copper phthalocyanine marker components and analyte components (theophylline, in this instance). While BSA is here described as the carrier, any similarly functionalized carrier species would suffice.

Marker component: selection and conjugation. Copper phthalocyanine 9 was selected as a potential marker component for the analyte conjugate due to its high molar absorptivity ($\gamma_{max}$ 678.5 nm, $\epsilon$=218,500 in chloronaphthalene). *J. Chem. Soc.*, 2466, 1957. A modified version 10, rendered both water-soluble by sulfonation and reactive by conversion to a dichlorotriazinylaminoethane sulfonamide, is readily available in crude form from several dye manufacturers (e.g., MX-G; Pro Chemical and Dye, Inc., Somerset, Mass.).

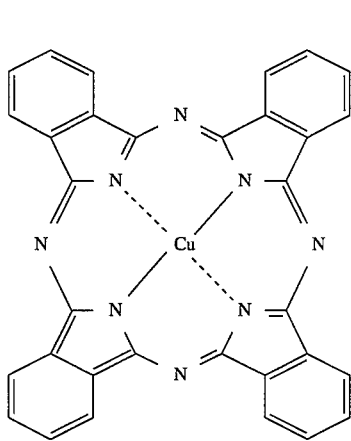

(9)

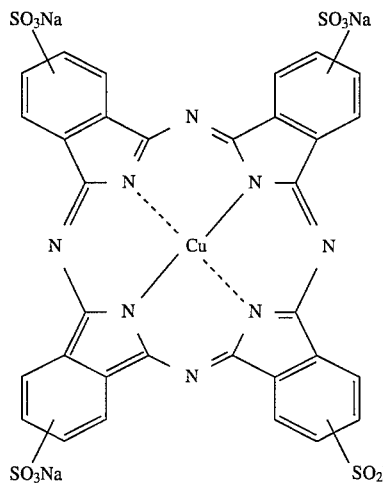

(10)

In spite of the high molar absorptivity of the parent copper phthalocyanine compound 9, we found that the dichlorotriazinylethylene diamine sulfonamide derivative 10 (hereinafter referred to as "CuPe") displayed an $\epsilon$ of 34,615 at $\gamma_{max}$ 666 nm in pH=8 phosphate buffer. Purification by column chromatography (silica, Dowex, cellulose Sephadex) or high performance liquid chromatography (HPLC) led to only at 15% increase in $\epsilon$, suggesting that factors other than impurities were responsible for the observed decrease in molar absorptivity ($\epsilon$). Related compounds are found to aggregate to form dimers and/or higher oligomers, with a dramatic decrease in $\epsilon$, when dissolved in aqueous solution at a variety of pH's and temperatures. *Aust. J. Chem.* 25:1661–1667, 1972. The bulk of such aggregates are dimers, (CuPc)$_2$, and so are referred to hereinafter as such.

Compound 10 was linked to bovine serum albumin (BSA) under reaction conditions analogous to those described in *J. Immunol. Meth.* 13:305, 1976, for optimal binding of dichlorotriazinylaminofluorescein to IgG. To a stirred solution of BSA (25 mg, 3.6×10$^{-4}$ mmol) in pH=8 phosphate buffer (2.0 ml) was added compound 10 (100 mg, 3.6×10$^{-2}$ mmol). The mixture was stirred at 25° C. for 22 hours and then filtered through Sephadex G-25 with pH=8 phosphate buffer (10.0 ml). The filtrate was concentrated by Are icon ultrafiltration (50 K; 600 ml pH=8 phosphate buffer, 600 ml distilled H$_2$O) and lyophilized to yield conjugate 11 (22 mg) as a blue solid with $\epsilon_{670}$=400,000, assuming a MW=80,000 for conjugate 11.

BSA—[(CuPc)$_2$]$_{10}$         (11)

Related conjugates were prepared as shown in the following Table:

| [BSA] | Eq(10)$^+$ | [(10)] | ml Buffer | Time | Eq(10)/ BSA* | Solubility |
|---|---|---|---|---|---|---|
| 2.9 × 10$^{-5}$ | 103 | 3 × 10$^{-3}$ | 1.0 | 1 h | 0.8 | v |
| 3.6 × 10$^5$ | 8 | 3 × 10$^{-4}$ | 10.0 | 22 h | 0.9 | v |
| 2.9 × 10$^{-5}$ | 34 | 1 × 10$^{-3}$ | 1.0 | 20 h | 5 | v |
| 1.8 × 10$^{-4}$ | 100 | 2 × 10$^{-2}$ | 10.0 | 22 h | 10 | v |
| 2.5 × 10$^{-4}$ | 497 | 1 × 10$^{-1}$ | 10.0 | 52 h | 19 | s |

Referring to the Table, the number of dimers of compound 10 per BSA molecule, Eq(10)/BSA, was determined, after purification, using $\epsilon$=40,000 per dimer and assuming a molecular weight of 70,000. All the conjugates were highly water soluble (v), with the exception of the last entry(s) in the table. The binding of approximately 19 dimers substantially decreased the water solubility of the BSA carrier.

Ready visualization (A>0.1) of most therapeutic drug analytes in a test solution containing the dimer-linked BSA (based upon an $\epsilon$ of 40,000 per dimer unit), requires the binding of at least 8 dimers of 10 per carrier. Such a sensitivity would allow the detection of analytes such as theophylline (10–100 ng/ml blood serum) but not analytes at concentrations in test fluid below on the order of 10 ng/ml, such as digoxin (0.5–2 ng/ml). In contrast, the corresponding monomer-linked BSA (based upon conjugation with eight monomers and an $\epsilon$ of 200,000 per monomer unit; see below) would expand the lower detection limit by a factor of five ($\epsilon_{monomer}$=5$\epsilon_{dimer}$) to encompass analytes occurring at concentrations in the 2 to 20 ng/ml range.

Aggregated copper phthaloeyanine derivatives are reported to disaggregate in aqueous solutions containing urea and thiourea (*Aust. J. Chem.* 26:1545, 1973) or solvents such as acetone (*Aust. J. Chem.* 25:1661–1667, 1972). Our attempts to either disaggregate the bound dimer from conjugates like 11 or prepare the monomeric analog of 11 were unsuccessful in urea. However, conjugation of BSA to 10 in certain acetone:buffer media led to the formation of predominantly monomeric copper phthalocyanine-linked BSA 12 with $\epsilon 670$ greater than 2×10$^6$.

BSA—(Cupc)$_{10}$         (12)

The order of addition as well as the ratio of acetone:buffer proved to be very important in optimizing the coloring of the conjugates. Optimum pigmentation was achieved when the copper phthalocyanine derivative 10 was added to a solvent system composed of greater than 50 percent acetone in pH=8 phosphate buffer prior to the gradual addition of dry BSA. A representative synthesis follows. BSA (75 mg, 1.1×10$^{-3}$ mmol) was added gradually to a stirred solution of compound 10 (109 mg, 1.1×10$^{-1}$ mmol) in a 70:30 mixture of acetone (87.0 ml) and pH=8 phosphate buffer (37.0 ml). The mixture was stirred at 25° C. for 48 hours, allowed to stand 24 hours, and then filtered through Sephadex G-25 with pH=8 phosphate buffer (30.0 ml). The liltrate was purified and concentrated by Amicon ultrafiltration (50 K; 3.0 L pH=8 phosphate buffer, 2.0 L distilled $H_2O$), and lyophilized to yield conjugate 12 (17 mg) as a dark blue solid with $\epsilon_{670}$=2,100,000, assuming a MW of 80,000 for 12.

Monomeric phthalocyanines can be similarly linked to other amine-bearing proteins, such as antibodies and antigens, to provide colored reagents useful for immunoassays generally. Aluminum phthalocyanine derivatives, in addition to being suitable chromogens, are advantageously luminescent as well.

Ligand component: biotinylation. Marker-labeled conjugates 11 and 12 were biotinylated with N-hydroxysuccinimidyl biotin (NHS-biotin) as described in the following representative protocol. To a stirred solution of conjugate 11 (5.0 mg, $6.3 \times 10^{-5}$ mmol) in pH=7 PBS (100 μL) was added NHS-biotin (0.4 mg, $1.3 \times 10^{-3}$ mmol) and a trace of $^3$H-NHS-biotin in dimethylformamide (DMF) (100 μL) and pH=7 PBS (20 μL). The mixture was stirred at 25° C. for two hours and then filtered through Sephadex G-25 with distilled $H_2O$ (600 μL) to yield biotinylated conjugate 13 as a clear blue solution. The extent of radiolabel incorporation indicated that each molecule of 13 was biotinylated with an average of 10 biotin molecules.

$(Biotin)_{10}$—BSA—$[(CuPc)_2]_{10}$ (13)

Preliminary experiments conducted with such highly biotinylated conjugates of 11 and 12 revealed that neither species had any avidin-binding efficiency. Using the procedure described above, we biotinylated conjugates 11 and 12 with a commercially available chain-extended biotin (sulfosuccinimidyl 6-biotinamidohexanoate; Pierce Chemical Co., Rockford, Ill.) to produce the analogous biotinylated species bearing 15 and 12 biotins, respectively. The resulting conjugated species were found to possess the requisite affinity for avidin.

Analyte component: tethered theophylline derivative. A tethered theophylline derivative was prepared for conjugation with protein, for use in an analyte conjugate to assay for theophylline in blood serum. First, theophylline acid 14 was prepared as described in *Res. Comm. Chem. Path. Pharm.* 13:497, 1976. A solution of 1.0 g (5.9 mmol) 5,6-diamino-1,3-dimethyluracil hydrate and 1.34 g (11.8 mmol) glutaric anhydride in 10.0 ml N,N-dimethylaniline was heated at 200° C. for three hours under nitrogen. After cooling to room temperature, the crystals that formed were collected by filtration. The crystals were washed with benzene and recrystallized from water. Theophylline acid 14 was isolated as white granules, 700 mg (45%).

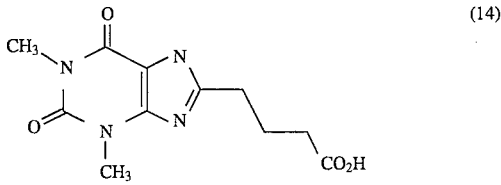

(14)

To a solution of 50 mg (0.188 mmol) acid 14, 4.0 ml pyridine, and 1.0 ml dioxane was added 43.2 mg (0.225 mmol) 1-ethyl-3-(3-dimethylaminopropyl) carbodiimide. The solution was stirred for one hour at room temperature. A solution of 35 mg (0.20 mmol) mono-t-butylcarbamate of 1,3-diamino-propane in 1.0 ml dioxane was added, and the resulting solution was stirred overnight. The reaction mixture was diluted with 10 ml methylene chloride, washed with dilute aqueous hydrochloric acid, dried over sodium sulfate and concentrated. Compound 15 was isolated as a white crystalline solid, 70 mg (88%).

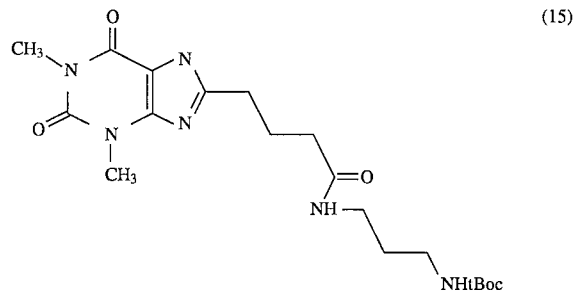

(15)

To 50 mg (0.118 mmol) carbamate 15 was added 1.0 ml ice-cold trifluoroacetic acid/methylene chloride (1:3). The solution was stirred at 0° C. for one hour. Removal of solvent gave amine 16 as a clear, colorless oil, 36 mg (96%).

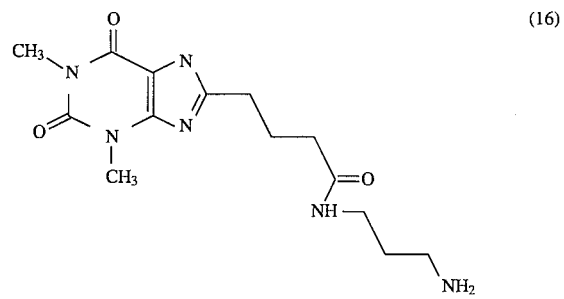

(16)

To a solution of 40.8 mg (0.118 mmol) succinimidyl 4-(N-maleimido-methyl) cyclohexane-1-carboxylate (SMCC) in 1.0 ml DMF was added 36 mg (0.112 mmol) amine 16 in 1.0 ml DMF. The resulting solution was stirred overnight at room temperature. The reaction mixture was diluted with 10 ml methylene chloride, washed with 3–10 ml portions of water, and dried over magnesium sulfate. Removal of solvent gave maleimide 17 as a crystalline solid, 38 mg (63%).

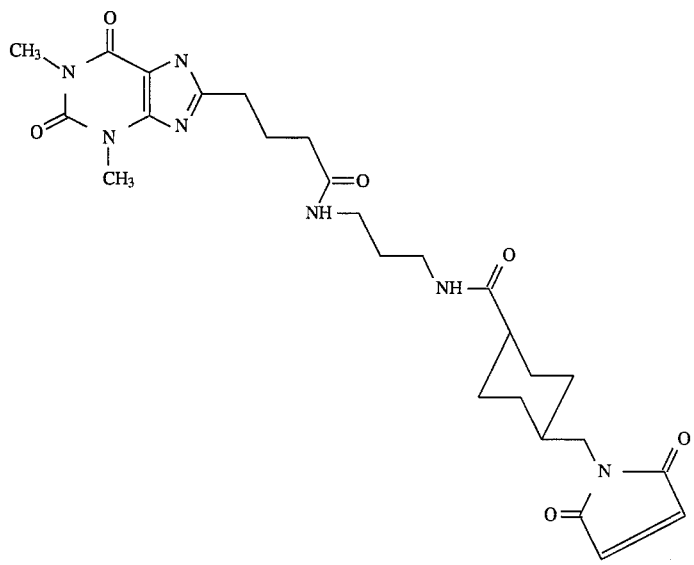

(17)

Theophylline derivative 17 is suitable for conjugation to sulfhydryl bearing species such as the BSA derivatives prepared below. Sufficient length has been built into this tether to maximize the interaction of the theophylline (analyte) component of the analyte conjugate with the antibody (analyte binding partner). To assure the recognition of the theophylline-protein conjugate by the antibody, the immunogen should mimic the analyte conjugate, that is, the tether point to theophylline should be consistent for both purposes.

Incorporation of sulfhydryl groups into BSA. To a solution of 5.0 mg ($7.58 \times 10^{-5}$ mmol) BSA in 1.0 ml PBS (pH7) was added the desired number of equivalents of N-succimidyl 3-(2-pyridyldithio)-propionate (SPDP) as a solution in absolute ethanol. After one hour at room temperature, the solution was filtered through Sephadex G-25.

To the resulting solution of the BSA/SPDP conjugate was added 1.2 mg ($7.58 \times 10^{-3}$ mmol) dithiothreitol (DTT). After 30 minutes at room temperature, the sulfhydryl (SH) content of the protein was assayed by measuring the absorbance of 2-thiopyridone at 343 nm. Representative results are shown below.

| Eq. SPDP | SH/BSA |
|---|---|
| 5 | 4 |
| 10 | 6 |
| 25 | 13 |
| 50 | 28 |

Conjugation of analyte component to BSA. The above BSA/SPDP conjugates bearing free sulfhydryl groups were reacted with theophylline analog 17 as follows. To a solution of 30 mg ($4.55 \times 10^{-4}$ mmol) BSA/SPDP conjugate (SH/BSA determined to be 3) was added 30 equivalents ($1.37 \times 10^{-2}$ retool) theophylline maleimide 17. After stirring overnight at room temperature, the reaction mixture was filtered through Sephadex G-25 and dialyzed against distilled water. Lyophilization gave 25 mg of a BSA/theophylline conjugate. Determination of 3 theophylline haptens per BSA was made by absorbance measurement at γ280 nm.

Construction of exemplary analyte conjugates. In the analyte conjugate, separate marker, ligand, and analyte components may be bound directly to a single carrier molecule. A representative analyte conjugate 18, shown schematically below, is preferably formed by covalently binding monomeric phthalocyanines to BSA, followed by biotinylation of the BSA and conjugation of theophyllines to the BSA, all as described above.

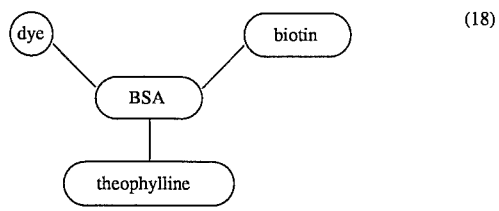

(18)

The biotin or other designated ligand component may, of course, be omitted from the analyte conjugate.

Two embodiments of the analyte conjugate which employ pairs of carrier molecules are shown below.

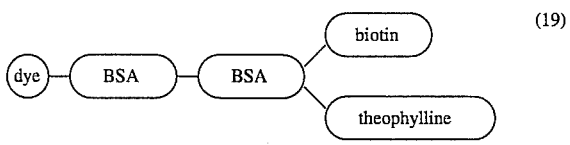

(19)

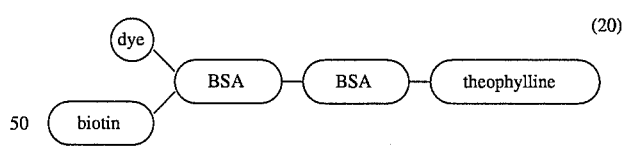

(20)

The preparation of these analyte conjugates follows the protocols described above; namely, dye binding, biotinylation, and theophylline conjugation to BSA. Formation of analyte conjugate 19 involves the linking of a BSA bearing phthalocyanine components to a BSA bearing blotins and theophyllines. Similarly, conjugate 20 is formed by linking a biotinylated, dye-labeled BSA to a BSA to which theophyllines have been conjugated. The BSA-BSA link is accomplished by introduction of sulfhydryl groups into one of the BSA components, as described above, and the incorporation of functionalities reactive toward sulfhydryls, such as alpha-iodoacetates or maleimides, into the other BSA component.

An extension of this methodology results in the modular analyte conjugate 21 represented schematically below.

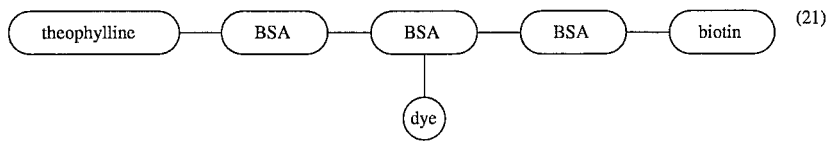
(21)

The preparation of the individual BSA conjugates and the assembly of the BSA links are as described above.

Avidinized analyte conjugate. In a complementary embodiment, the analyte conjugate may contain an avidin ligand component. Two representative avidinized analyte conjugates are shown schematically below.

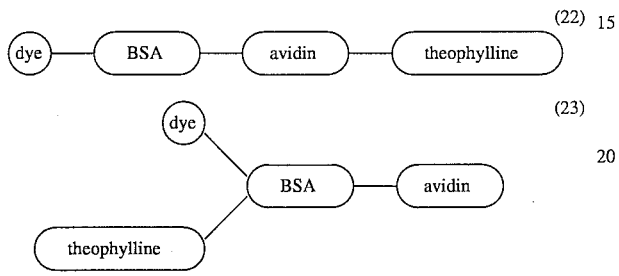
(22)
(23)

Preparation of 22 and 23 follow from the chemistries described above. For 22, a dye-BSA conjugate is covalently linked to an avidin-theophylline conjugate in a manner analogous to the linking of BSA conjugates described above. The formation of 23 involves the linking of avidins to a BSA bearing both dyes and theophyllines.

BSA protected dye-BSA conjugate. The hydrophobicity of the copper phthalocyanine components of the above analyte conjugates may lead to nonspecific binding of the conjugates to some surfaces, such as polyethylene and other plastics. This potential problem is alleviated by blanketing the dye-BSA complexes with additional BSA.

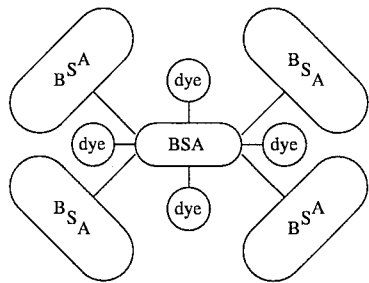
(24)

The BSA protected version (24) of the dye-BSA conjugate utilizes the chemistries described above for linking BSA conjugates and BSA-avidin conjugates. Specifically, a dye-BSA complex is treated with SMCC to yield a dye-BSA conjugate bearing maleimide groups. To this complex is added an excess of BSA sulfhydryl groups with the maleimide groups on the dye-BSA conjugates results in the covalent binding of the two species to produce BSA-protected dye-BSA conjugates such as 24, which may be readily purified by size exclusion chromatography, and to which ligands such as biotin and analyte components such as 17 may be bound to produce the analyte conjugate.

BSA-blanketed conjugates such as 24 can also be used to diminish oxygen quenching of luminescence, e.g., where metalloporphyrins are used as the marker component, by sequestering such markers ("dye") from contact with ambient oxygen. For example, by shielding oxygen-quenchable luminescent markers such as platinum porphyrins (see Example 7) within the hydrophobic core of proteinaceous conjugate 24, oxygen is physically excluded from interacting with the metal in its excited state. Quenching of the luminescent signal by vibrational deactivation, such as is known to occur in lanthanide porphyrins, is analogously reduced by complexing, e.g., a ytterbium porphyrin within a protective conjugate such as 24.

EXAMPLE 9

Luminescent Probes

The unique luminescent properties of the platinum (Pt) and ytterbium (Yb) porphyrin derivatives make them attractive reporting groups in immunoassay systems. Like aluminum phthalocyanine, the platinum and ytterbium porphyrins exhibit large Stokes shifts and emit at wavelengths (650 and 975 mm, respectively) beyond those of endogenous physiological fluorophores. Unlike aluminum phthalocyanine, the emissions of Pt and Yb porphyrin are long-lived and furthermore can be selectively quenched in solution. When coupled directly or indirectly to analytes such as theophylline, the porphyrin derivatives can be used as analyte conjugates in either homogeneous or heterogeneous immunoassays. For such uses, the porphine meso-carbon rings should be substituted with the aforesaid water-solubilizing groups R; representative examples are tetracarboxyltetraphenylporphyrin and tetrasulfotetraphenylporphyrin.

Homogeneous immunoassay: Upon antibody binding of either the Pt or Yb porphyrin analyte conjugate, some protection of the metallo porphyrin results. For the Pt species, the antibody provides protection from oxygen quenching of phosphorescence. In the case of the Yb derivative, the antibody serves to protect the probe from the aqueous environment and luminescence quenching by vibrational deactivation of the excited metal. As a result, in contrast to the free (and quenched) analyte conjugates present in solution, the antibody-bound analyte conjugates are luminescent. The amount of luminescence is measured and related to the amount of analyte present in the test sample.

Heterogeneous immunoassay: The analyte conjugates of the Pt and Yb porphyrins are constructed such that they are not susceptible to luminescence quenching. Luminescent derivatives require that the metal centers be surrounded by moieties that sterically prevent interactions with oxygen in the case of Pt and with water for Yb. The exemplary protected versions of the analyte conjugates 18 through 24 provide protection in aqueous solution from both oxygen and water (vibrational) quenching. Incorporation of these luminescent species into polymeric microspheres using techniques described in Example 8 also prevent oxygen and water quenching. The assay quantitation then requires the separation of antibody-bound and free analyte conjugate.

Time resolution: The Pt and Yb porphyrin reagents possess luminescent lifetimes on the order of microseconds. The long-lived emission makes these probes ideal candidates for time-resolved systems. Time-gated detection of these reagents at relatively long times eliminates background fluorescence (in the nanosecond time frame) from the matrix and the scattering events associated with excitation. The measurement of the luminescent signal against essentially no background significantly increases assay sensitivity.

While the preferred embodiments of the invention have been illustrated and described, it is to be understood that, within the scope of the appended claims, various changes can be made therein. Hence, the invention can be practiced in ways other than those specifically described herein.

What is claimed is:

1. A reagent composition comprising a physiological analyte and a phthalocyanine derivative, the phthalocyanine derivative being covalently conjugated in monomeric form in the reagent composition and having absorbance in both the red and blue portions of the spectrum, wherein the ration of the relative heights of the maximum red and blue absorbance peaks of the reagent composition. A(red)/A(blue), is greater than about 1.5.

2. The reagent composition of claim 1, wherein the physiological analyte is selected from the group consisting of drugs, drug metabolites, hormones, peptides, nucleotides, neurotransmitters, cholesterol, growth factors, oligonucleotides, peptides, antibodies, antigen-binding fragments, serum proteins, enzymes, polynucleotides, intracellular organelles, cell surface antigens, avidin, biotin, binding proteins, nucleic acids, membrane probes, and nucleic acid probes.

3. The reagent composition of claim 1, wherein the phthalocyanine derivative is metallated with aluminum, copper, silicon, phosphorus, gallium, germanium, cadmium, scandium, magnesium, tin, or zinc.

4. The reagent composition of claim 1, wherein the phthalocyanine derivative comprises one or more substituents selected from among sulfonic acid, sulfonate, carboxylic acid, carboxylate, phosphoric acid, phosphate, phosphonate, hydroxy, phenoxy, amino, ammonium, and pyridinium substituents.

5. The reagent composition of claim 1, wherein the phthalocyanine derivative is conjugated in monomeric form via an enzyme-cleavable linkage with the physiological analyte.

6. The reagent composition of claim 1, wherein the physiological analyte comprises a hydrophilic component that substantially envelops the monomeric phthalocyanine derivative.

7. The reagent composition of claim 1, wherein the ratio of the relative heights of the maximum red and blue absorbance peaks of the reagent composition, A(red)/A(blue), is greater than or equal to 1.75.

8. The reagent composition of claim 1, wherein the ratio of the relative heights of the maximum red and blue absorbance peaks of the reagent composition, A(red)/A(blue), is greater than or equal to 2.

* * * * *

UNITED STATES PATENT AND TRADEMARK OFFICE
CERTIFICATE OF CORRECTION

PATENT NO. : 5,494,793  Page 1 of 3
DATED : February 27, 1996
INVENTOR(S) : D.C. Schindele et al.

It is certified that error appears in the above-identified patent and that said Letters Patent is hereby corrected as shown below:

Title page, item

| | | |
|---|---|---|
| [63] | Related U.S. App'n Data | "198803" should be --1988 abandoned-- |
| [63] | | after "Sep. 8, 198803[sic]," insert --and is a continuation-in-part of international application No. PCT/US87/03226, filed Dec. 11, 1987,-- |
| [63] | Related U.S. App'n Data | "198903" should be --1989-- |
| [56] | Other Publications | Insert --Martin, P.C., et al., "Effects of ligands, solvent, and variable sulfonation on dimer formation of aluminum and zinc phthalocyaninesulfonates," *Inorganic Chemistry*, 30:3305-3309, 1991.-- |
| [57] | Abstract | "+" should be --+3-- |

| Column | Line | |
|---|---|---|
| 1 | 8 | "309,454" should be --309,453-- |
| 4 | 43 | "+" should be --+3-- |
| 8 | 48 | "+" should be --+3-- |

UNITED STATES PATENT AND TRADEMARK OFFICE
CERTIFICATE OF CORRECTION

PATENT NO. : 5,494,793

DATED : February 27, 1996

INVENTOR(S) : D.C. Schindele et al.

It is certified that error appears in the above-identified patent and that said Letters Patent is hereby corrected as shown below:

| COLUMN | LINE | |
|---|---|---|
| 9 | 62 | "phthaloeyanine" should be --phthalocyanine-- |
| 21 | 14 | "phthaloeyanine" should be --phthalocyanine-- |
| 24 | 13 | "patter" should be --parter-- |
| 24 | 50 | "none missive" should be --nonemissive-- |
| 28 | 44 | "phthaloeyanine" should be --phthalocyanine-- |
| 29 | 28 | "CuPe" should be --CuPc-- |
| 29 | 47 | "Are icon" should be --Amicon-- |
| 30 | 43 | "phthaloeyanine" should be --phthalocyanine-- |
| 30 | 55 | "(Cupc)" should be --(CuPc)-- |
| 34 | 56 | "blotins" should be --biotins-- |
| 36 | 22 | "phthaloeyanine" should be --phthalocyanine-- |
| 36 | 25 | "phthaloeyanine" should be --phthalocyanine-- |

UNITED STATES PATENT AND TRADEMARK OFFICE
CERTIFICATE OF CORRECTION

PATENT NO. : 5,494,793
DATED : February 27, 1996
INVENTOR(S) : D.C. Schindele et al.

It is certified that error appears in the above-identified patent and that said Letters Patent is hereby corrected as shown below:

| COLUMN | LINE | |
|---|---|---|
| 36 | 33 & 34 | "tetraearboxlyltetraphenylporphyrin" should be --tetracarboxyltetraphenylporphyrin-- |
| 36 | 39 | "ease" should be --case-- |
| 36 | 42 | "deaetivation" should be --deactivation-- |
| 37 | 14 | "ration" should be --ratio-- |
| 37 | 16 | "composition." should be --composition,-- |

Signed and Sealed this

Twelfth Day of November, 1996

Attest:

BRUCE LEHMAN

*Attesting Officer*       Commissioner of Patents and Trademarks